US010688452B2

(12) United States Patent
Roche Rebollo et al.

(10) Patent No.: US 10,688,452 B2
(45) Date of Patent: Jun. 23, 2020

(54) METHODS, DEVICES, SYSTEMS AND KITS FOR PREPARING COMPOSITIONS FOR CARE AND REPAIR OF VARICOSE VEINS

(71) Applicant: Vascular Barcelona Devices, S.L., Barcelona (ES)

(72) Inventors: Enrique Roche Rebollo, Barcelona (ES); Antoni Puig Domenech, Sant Cugat Del Valles (ES); Guiu Llusà Meléndez, Barcelona (ES); Jordi Puig Herrera, Barcelona (ES)

(73) Assignee: VASCULAR BARCELONA DEVICES, S.L., Barcelona (ES)

( * ) Notice: Subject to any disclaimer, the term of this patent is extended or adjusted under 35 U.S.C. 154(b) by 10 days.

(21) Appl. No.: 15/363,906

(22) Filed: Nov. 29, 2016

(65) Prior Publication Data

US 2017/0144115 A1    May 25, 2017

Related U.S. Application Data

(63) Continuation of application No. PCT/EP2015/062265, filed on Jun. 2, 2015.

(30) Foreign Application Priority Data

Jun. 3, 2014  (ES) .................................. 201430845

(51) Int. Cl.
*B01F 13/08* (2006.01)
*B01F 3/04* (2006.01)
(Continued)

(52) U.S. Cl.
CPC .......... *B01F 3/04992* (2013.01); *A61K 9/122* (2013.01); *A61K 31/08* (2013.01);
(Continued)

(58) Field of Classification Search
CPC .................................................. B01F 13/0818
(Continued)

(56) References Cited

U.S. PATENT DOCUMENTS 3,575,536 A * 4/1971 Jacobs ..................... B67D 1/10
310/104
3,649,465 A   3/1972 Scharf et al.
(Continued)

FOREIGN PATENT DOCUMENTS

DE    4122476 A1    1/1993
EP    0149529 A2    7/1985
(Continued)

OTHER PUBLICATIONS

International Search Report in corresponding PCT Application No. PCT/EP2015/062265, dated Dec. 15, 2015.
(Continued)

*Primary Examiner* — David L Sorkin
(74) *Attorney, Agent, or Firm* — Edell, Shapiro & Finnan, LLC

(57) ABSTRACT

The present disclosure relates to a container for the production of a foamed sclerosant composition, to kits and systems including such a container, to methods for preparing a foamed sclerosant composition using such containers, and to a foamed sclerosant compositions obtainable by such methods. In an aspect, the container comprises a container body and a mixing element disposed in the container body, such that a foaming space is defined in an interior of the container body between the sidewalls and the mixing element. The mixing element may be configured to be operatively coupled with a rotating actuator without the actuator reaching the foaming space.

17 Claims, 18 Drawing Sheets

(51) Int. Cl.

| | | |
|---|---|---|
| *B01F 7/00* | (2006.01) | |
| *B01F 7/16* | (2006.01) | |
| *B01F 13/00* | (2006.01) | |
| *A61K 9/12* | (2006.01) | |
| *A61K 31/08* | (2006.01) | |
| *B01F 15/00* | (2006.01) | |
| *B01F 15/02* | (2006.01) | |

(52) U.S. Cl.
CPC ...... *B01F 3/04453* (2013.01); *B01F 7/00408* (2013.01); *B01F 7/00466* (2013.01); *B01F 7/00558* (2013.01); *B01F 7/162* (2013.01); *B01F 7/1695* (2013.01); *B01F 13/0022* (2013.01); *B01F 13/0818* (2013.01); *B01F 15/0085* (2013.01); *B01F 15/026* (2013.01); *B01F 15/0237* (2013.01); *B01F 2215/0032* (2013.01)

(58) Field of Classification Search
USPC ...................................... 366/182.4, 273, 274
See application file for complete search history.

(56) References Cited

U.S. PATENT DOCUMENTS

| | | | | |
|---|---|---|---|---|
| 3,838,034 | A * | 9/1974 | Groves ................... | G01N 7/00 204/403.05 |
| 4,614,437 | A | 9/1986 | Buehler | |
| 4,759,635 | A * | 7/1988 | MacMichael ....... | B01F 13/0818 366/247 |
| 5,676,962 | A * | 10/1997 | Cabrera Garrido .... | A61K 9/122 424/423 |
| 8,469,924 | B2 * | 6/2013 | Nguyen ........... | A61B 17/00008 604/89 |
| 2007/0053238 | A1 | 3/2007 | Kocienski | |
| 2007/0189115 | A1 * | 8/2007 | Yaniv .................. | B01F 13/0827 366/274 |
| 2010/0046323 | A1 | 2/2010 | Tien et al. | |
| 2011/0042944 | A1 | 2/2011 | Johns et al. | |

FOREIGN PATENT DOCUMENTS

| | | | |
|---|---|---|---|
| EP | 2578308 | A2 | 4/2013 |
| ES | 2147111 | A1 | 8/2000 |
| ES | 2247898 | A1 | 3/2006 |
| ES | 2254177 | T3 | 6/2006 |
| ES | 2354695 | T3 | 3/2011 |
| FR | 2449473 | A1 | 9/1980 |
| GB | 1493776 | A | 11/1977 |
| WO | 9500120 | A1 | 1/1995 |
| WO | 0066274 | A1 | 11/2000 |
| WO | 2005048976 | A2 | 6/2005 |
| WO | 2006120461 | A1 | 11/2006 |
| WO | 2007114934 | A2 | 10/2007 |
| WO | 2015185554 | A2 | 12/2015 |

OTHER PUBLICATIONS

Cabrera, J., et al., "Treatment of Varicose Long Saphenous Veins of Sclerosants in Microfoam Form With: Long-term Outcomes," Phlebology, vol. 15; 19-23 (2000).

Morrison, N., et al., "Comparisons of side effects using foam air and carbon dioxide for endovenous chemical ablation," Journal of Vascular Surgery, vol. 47(4):830-836 (Apr. 2008).

Morrison, N., "Studies on safety of foam sclerotherapy," Foam Sclerotherap: A Textbook, John Bergan, Van Le Cheng. pp. 183-193 Royal Society of Medicine Press Ltd. (2008).

Schadeck, M., and F.A. Allaert, "Duplex scanning in the mechanism of the sclerotherapy: Importance of the spasm," Phlebology, Suppl. 1: 574-576 (1995).

Tessari, L., et al., "Preliminary experience with a new sclerosing foam in the treatment of varicose veins," Dermatol Surg, vol. 27 (1): 58-60 (Jan. 2001).

van den Bos, R., et al., "Endovenous therapies varicosites of lower extremity. A meta-analysis,". . . J Vasc Surg, vol. 49 (1): 230-239 (Jan. 2009).

European Patent Office Examination Report in corresponding European Application No. 15729370.5, dated Jun. 21, 2018.

* cited by examiner

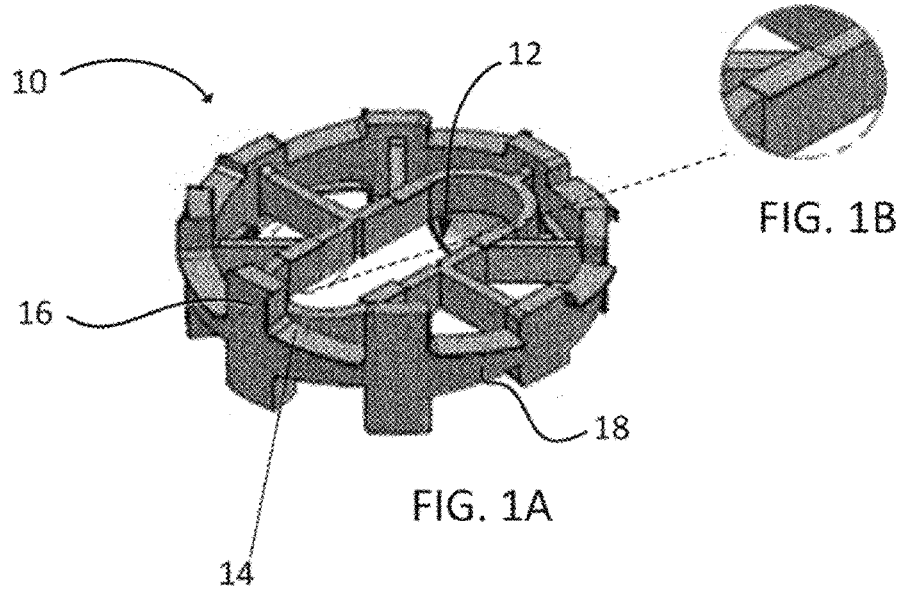
FIG. 1B
FIG. 1A
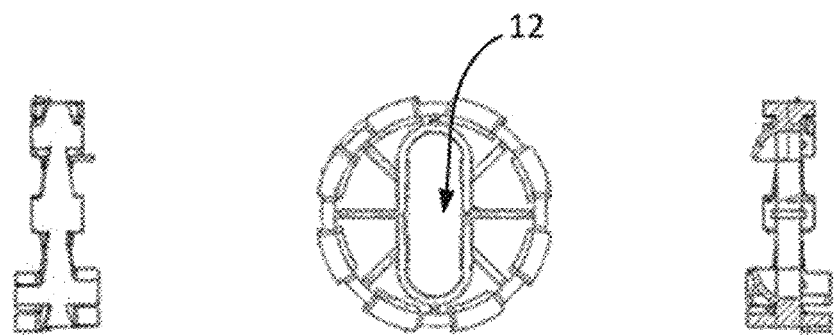
FIG. 1C  FIG. 1D  FIG. 1E

METHODS, DEVICES, SYSTEMS AND KITS FOR PREPARING COMPOSITIONS FOR CARE AND REPAIR OF VARICOSE VEINS

CROSS REFERENCE TO RELATED APPLICATIONS

This application is a continuation of International Application No. PCT/EP2015/062265, filed on Jun. 2, 2015, which claims priority under 35 U.S.C. § 119 to Application No. ES P201430845 filed on Jun. 3, 2014, the entire contents of which are hereby incorporated by reference.

FIELD OF THE INVENTION

The present disclosure is related to the technical field of vascular medicine, more particular to the field of treatments for varicose veins and other vascular problems such as e.g. spider veins and/or haemorrhoids.

Specifically, the present disclosure relates to devices, systems, kits and methods for obtaining a foam, which can be used for the treatment of the affected veins. The present invention further relates to the composition of the foam itself obtained by any of the procedures described throughout present disclosure, as well as the use of the devices, systems and kits in order to treat varicose veins and other vascular problems such as e.g. spider veins and/or haemorrhoids.

BACKGROUND

Varicose veins occur when the venous valves (which prevent the backflow of blood) do not work properly. As a result, the vein walls are weakened, and they can become deformed and dilated. Due to the fact that the valves do not work properly, the blood may recirculate and short-circuits may be created. Subsequently, the veins may become progressively dilated. In this way, the varicose veins can become more visible, and can be full of bends and become more voluminous. The evolution of this pathology may lead to consequences beyond the cosmetic ones, such as discoloration of the skin, pain and swelling of the extremities due to the effect of the venous hypertension.

According to the Spanish Society of Angiology and Vascular Surgery (SEACV) in Spain, varicose veins affect from 30 to 33% of the adult population in industrialized countries.

The veins most commonly affected are those located in the legs, although varicose veins may occur interiorly as well: e.g. varicose veins in the esophagus, around organs located in the pelvis (pelvic and ovarian varicose veins) or at or near the most distal part of the digestive tube, near the anus (haemorrhoids).

Nowadays, there are many different treatments and/or strategies in order to mitigate or eliminate these problems. Among them, we can find surgical methods. These surgical methods are related to the surgical extraction of the affected veins using classical surgery. This technique has been employed for over 100 years. This technique is based on making different skin incisions with subsequent clamping, ligation and stripping of the venous segments affected. This technique is performed under spinal anesthesia (infiltration of the spinal space) in order to obtain the anesthesia of both limbs, as well as with local or nerve block anesthesia to anesthetize more limited areas.

In the late 1990's, there was an important advance regarding the treatment of this disease because the varicose veins were treated with less invasive techniques such as the endovenous techniques. Among these new methods, it is important to highlight intravenous procedures that apply heat through a catheter (endolaser or radio frequency systems).

These systems were able to reduce injuries due to the fact that the methods are usually performed under ultrasound guidance. The effect to the veins was produced by the release of heat or electricity from inside the vein, thus an internal injury into the vein may be produced. This way, a thrombosis of the veins was achieved.

The other technique developed was sclerotherapy by injection of a sclerosing foam. This technique (compared to the "Endolaser" or radiofrequency therapies) is even less aggressive, less painful, and needs no anesthesia (R Van den Bos et al. *Endovenous therapies varicosites of lower extremity. A meta-analysis*. J Vasc Surg 2009 January; 49 (1): 230-9).

In summary, in the late 1990's and early 2000 a trend was found to minimize the aggressiveness varicose veins treatments. Of all the new emerged techniques, the sclerotherapy seems to be the less invasive and the one which can be applied to practically any type of varicose veins.

For this reason, in recent years, this procedure has been developed a lot and it has been found a growing interest from the scientific community in order to obtain methods suitable for the manufacture of a foam in a safe and convenient way.

Sclerotherapy involves the injection of a liquid with the ability to irritate the vascular endothelium (a thin layer or lining inside the vein that is in contact with the bloodstream).

This drug or liquid medicine can become a foam when shaken. The products internationally approved for this use are lauromacrogol (also known named as polidocanol and commercially available as etoxiesclerol), and sodium tetradecyl sulfate.

The advantage of using such a product as a foam is based on the enhancement of its effect due to the larger contact surface with the endothelial wall. The larger contact surface offers the possibility of dose reduction. Also the visibility of the drug as a foam using ultrasounds through the ultrasound scanner is improved (Schadeck M, Allaert FA. *Duplex scanning in the mechanism of the sclerotherapy: Importance of the spasm*. Phlebology 1995; Suppl1: 574-576).

The effect produced by the foam on the endothelium involves the injury of the cell layer, thereby the thrombosis of its content is produced. Later, this vein suffers a fibrosis process (retraction and disposal) and the vein eventually may disappear after several months.

This process can be faster or slower depending on the size of the vein or the potency of the varicose agent. Therefore, it is sometimes necessary to apply several sessions on the vein.

Although there are several methods in order to eliminate or remove varicose veins, the less aggressive and disabling treatment so far, and the one which can be used for a wide variety of pathologies is the ultrasound-guided Foam Sclerotherapy using polidocanol or other sclerosing agents. Sclerotherapy is the less invasive treatment of varicose veins known today as it can be performed in a physician's office and in a completely ambulatory way. Therefore, the present disclosure is focused on the use of this technique.

Focusing on the past 50 years, one can find numerous bibliographic references using different products and techniques to treat varicose veins without surgery.

Orbach, in 1944, was one of the pioneers in the use of air injected into the vein to promote the effect of a sclerosing product. The appearance of the ultrasound and its implementation in the real-time study of the venous pathology was a revolution in the field of the phlebology.

In 1995, Dr. Juan Cabrera presented the results of the application of a foam that he had developed with his son, the pharmacist Juan Cabrera (Cabrera J. et al. *"Treatment of Varicose Long Saphenous Veins of Sclerosants in Microfoam Form With: Long—term Outcomes"*. Phlebology (2000) 15; 19-23). This foam was characterized by its density and high solubility thanks to the use of a mixture of physiological gases.

Furthermore, he managed to achieve a type of foam with very small and uniform bubble size, thanks to his method of using a mixer. By using a mixture of physiological gases, the foam had greater security and stability. This foam was called "microfoam" due to the small bubble size, uniformity and stability.

Shortly after, the maximum popularization of the sclerosing foam use came from Lorenzo Tessari (Tessari L., Cavezzi A., Frullini A., *Preliminary experience with a new sclerosing foam in the treatment of varicose veins*. Dermatol Surg 2001 January; 27 (1): 58-60) who published his experience using a foam easily manufactured through a procedure called *"The Tessari Method"*. The method consists in the agitation of a sclerosing liquid using two syringes connected via a three-way tap. By means of successive alternately movements with each of the syringes connected to the gas/liquid mixture, a mix of foam, located at the inner part of the syringe, was achieved. However, this manufacturing technique, in spite of being the most widespread is not the most effective, since a relatively unstable and heterogeneous foam is obtained.

In recent years numerous articles and papers have been published about safety profiles, side effects and potential complications arising from the use of these products. Thus, it appears demonstrated that the best foam used is the one whose gas is a mixture of $O_2/CO_2$ at different concentrations. With this arrangement, the solubility and diffusion in blood is very high as opposed to atmospheric gas foams. Additionally, the foam stability is linked to the size of the bubble. Also, it has been found that the foam is more stable when the bubble diameter is more homogeneous.

There are different patents related to the aforementioned therapies that describe and protect each one of the existing methods in the state of the art. Thus, we can find the Spanish patent ES2147111, relating to a device for the application of an anti-varicose treatment that is based upon injecting sclerosant products cooled to a very low temperature by carbonic liquid, and which is characterized by the fact that it is equipped with means for coupling and extracting liquid carbon from a tank that enables the liquid carbon to be applied at atmospheric pressure in a syringe containing the sclerosant product to be injected into the varicose vein.

Similarly, the international patent WO 95/00120 relates to an injectable microfoam that contains a sclerosant agent. The foam may be created by using a mixer on a sclerosing liquid.

Similarly, the patent ES 2 247 898 relates to the use of an injection of polydocanol in the form of foam for the painless removal of varicose veins by laser. This use consists of a combination of 1) prior treatment of the vascular injuries by injecting a hypermolar hyperalcoholic substance that can be injected into the vein; 2) injecting said substance in the form of a microfoam; and 3) applying to the veins the emission from an Nd-Yag laser in its basic emission (or applying any other laser that emits with a wavelength close to the resonant of the injected substance). In particular, this patent refers to said use when the substance used as the injectable substance is polidocanol in the form of microfoam. The injection of said hydroalcoholic substance in the form of microfoam makes it possible to reduce the fluidity of the laser by 40%.

The international application WO2006120461 is related to a device configured to facilitate the preparation of therapeutic foam e.g. for the treatment of varicose veins. A pressurised vial contains a sclerosant liquid, e.g. polidocanol solution, and a sterile gas which is readily absorbed by the body, e.g. carbon dioxide, oxygen or a mixture of these gases. The vial is provided either with a specialised stopper/seal into which a syringe nozzle may be inserted or alternatively a septum seal which may be penetrated by a hypodermic needle. The quantities of gas and liquid and the pressure in the vial are pre-set so that, on connection of a syringe to the vial, a predetermined volume of both gas and liquid is transferred to the syringe, with the intention that the syringe is then used to make a foam by known means. The use of the vial ensures that the ratio of gas to liquid in the foam is standardised, and also provides a convenient way of packaging the gas and liquid and of filling the syringe in a sterile manner.

The patent ES 2 254 177 describes therapeutic sclerosing microfoams, methods and devices that have an advantage in producing a consistent profile injectable foam with minimal input by the physician yet using high volume percentages of blood dispersible gases, thus avoiding use of potentially hazardous amounts of nitrogen. The method comprises passing a mixture of a physiologically acceptable blood dispersible gas and an aqueous sclerosant liquid through one or more passages having at least one cross-sectional dimension of from 0.1 to 30 microns, the ratio of gas to liquid being controlled such that a microfoam is produced having a density of between 0.07 g/mL to 0.19 g/mL and a half-life of at least 2 minutes.

ES 2 354 695 discloses a foam transfer device, for use with aerosol canister apparatus for producing a sclerosant foam for the treatment of, inter alia, varicose veins.

WO2005048976 discloses a therapeutic foam for the treatment of, inter alia, varicose veins comprising a sclerosing solution foamed with a physiological gas such as carbon dioxide, oxygen or a mixture thereof. The foam has a nitrogen content of less than 0.8%. It may be generated using a pressurized canister system incorporating a fine mesh of micron dimensions through which the gas and sclerosing liquid are passed to make the foam. Alternatively, the foam may be generated by passing gas and solution between two syringes through a fine mesh. Techniques are described for minimizing the amount of nitrogen in a canister or syringe based product. A technique for generating and delivering foam simultaneously using a syringe based device is also disclosed.

Another interesting document is WO 00/66274. The device includes a container in which the sclerosing liquid is deposited, in addition to connecting means to a propellant gas source. Said container is hermetically closed by a head piece in which a small diameter probe tube is inserted to reduce pressure, said tube extending inside the container and being closed by a valve, whose actuation causes the outflow of the foamed sclerosing agent through an outlet provided in the head piece as a result of the propellant gas.

As has already been mentioned, although there are a lot of manufacturing systems of sclerosing foam, the most common foam (and the one which is normally used around the world) is the foam obtained with the Tessari method. However, this method has many problems of standardization and homogenization. This system consists of mixing air flow with the selected liquid, either polidocanol or sodium tetradecyl sulfate (commercially known as Sotradecol®). This foam can have medium size bubbles, but of irregular size and it becomes unstable after a few seconds of its formation. Additionally, the use of atmospheric gas as a vehicle for the sclerosing foam limits the foam administrable per session.

As mentioned above, Dr. Juan Cabrera was the pioneer in using a physiological gas mixture which provides the foam high solubility. However, in recent years many other phlebologists and vascular surgeons have developed different foam manufacturing methods. Specifically, Nick Morrison showed the low rate of undesirable effects of a foam made with a mixture of $O_2/CO_2$ (Nick Morrison. *Studies on safety of foam sclerotherapy Foam Sclerotherapy.* John Bergan, Van Le Cheng. Pp. 183-193 Royal Society of Medicine Press Ltd. 2008). These gases have the advantage of being dissolved and diffused safely in our organism (Nick Morrison. *Comparisons of side effects using foam air and carbon dioxide for endovenous chemical ablation* J Vasc Surg. 2008 Jan. 31).

The manufacture of different types of foams using commonly used medications and drugs results in great variability of foams. According to the manufacturing method used, and depending on the gas composition and the sclerosing agent, a foam of better or worse quality can be obtained.

There is therefore a need to find devices, kits, systems and methods for obtaining quality foams which are safe and can be obtained in a relatively cheap manner.

SUMMARY

In a first aspect, a sterile container for the production of a foamed sclerosant composition is provided. The container comprises a container body having one or more sidewalls extending between a top and a bottom of the container body, and a mixing element disposed in the container body. Thereby a foaming space is defined in an interior of the container body between the sidewalls and the mixing element. The mixing element is configured to be operatively coupled with a rotating actuator without the actuator reaching the foaming space and the container comprises a valve suitable for the introduction of a liquid sclerosant composition in the foaming space.

According to this first aspect, a sterile container can be provided into which the sclerosant composition in liquid form can be introduced. A mixing element is an element which ultimately creates a foam by mixing the contents of the container. According to this aspect, the mixing element is disposed in the sterile environment of the container, i.e. no introduction of the element from the outside is necessary. Since the rotating actuator never enters into the foaming space, contamination of the foam can be reduced to a minimum. Rotation of the actuator nevertheless causes the mixing element to rotate within the container thus producing a foam.

Achieving an operative coupling between the actuator outside the foaming space and the mixing element may be achieved in a variety of ways. In some examples, the mixing element may be mechanically coupled with the rotating actuator. In this case, the mechanical coupling may be such that the actuator couples with a portion of the mixing element outside the foaming space.

In other examples, a mixing element may be magnetically coupled with the rotating actuator. A magnetic coupling may be achieved by the mixing element comprising a magnetic portion or element, and the actuator as well. The magnetic coupling may be achieved through the walls of the container.

The mixing element may be completely enclosed within the container body. The foaming space is thus not contaminated.

In yet further examples, mixing elements may be integrally formed with or attached to one or more walls of the container body. Also in this case, the mixing element(s) may be completely enclosed within the container body. The container itself may then be agitated. Also in this case, the foaming can be achieved in the sterile container with virtually no contamination.

In some examples, the mixing element may comprise a helical wire substantially arranged along a circle. Such a helical wire may be arranged at a distal end of a shaft of a mixing element. In other examples, the mixing element is a disc with teeth around its circumference. The disc could be attached at a distal end of a shaft with a mechanical coupling with the actuator, or could have a magnetic portion such that it can be actuated with a magnetic actuator such as a magnetic stirrer. In an example, a core of the disc may be made of magnetic material, whereas other portions of the disc are made of non-magnetic material, e.g. a polymer.

In some examples, the valve suitable for the introduction of a liquid sclerosant composition may be a one-way valve, arranged to open towards the interior of the container body. A one-way valve may allow a sclerosant composition to be injected or introduced into the container, but prevents the valve from opening. In some examples, a single valve may be used for both the introduction of the liquid sclerosant composition and for the introduction of a physiological gas. In other examples, a separate valve may be provided for the introduction of a physiological gas.

In the preparation of a foamed sclerosant composition, physiological gases may be used. Such a physiological gas may be a mixture of $CO_2$ and $O_2$. For example, a mixture of 50/50 may be used. A large proportion of $CO_2$ leads to quick absorption in the body. A large proportion of $O_2$ makes the foam more stable. In an alternative example, the maximum amount of $CO_2$ may be 70%, the physiological gases may thus be in a ratio of 70/30.

The use of physiological gases may be regarded as safer to the patient, than the use of (ambient) air. When large amounts of foam are to be injected, it is recommended to use physiological gases. The sterile containers according to these examples may thus be configured for their introduction.

In some examples, the container body further comprises an exit for extraction of the foamed sclerosant composition. Such an exit may be in the form of a tearable or frangible portion of the container body, e.g. of a sidewall or bottom of the container body. A syringe may thus be inserted into the container body in a safe and clean manner, without contaminating the foam. The same syringe may subsequently be used for injection of the foamed sclerosant composition into a patient's veins. If a tearable or frangible portion of the container is used, the container has to be disposed of after a single use.

In a further aspect, a kit for the preparation of a foamed sclerosant composition is provided. The kit comprises a container according to any of the examples herein described, and further comprises an introducer for the introduction of a physiological gas, the introducer defining a first channel for introducing of the physiological gas, and a second channel for evacuating a gas in the interior of the container body.

In some examples, a kit may further comprise a syringe for aspirating the foamed sclerosant composition and/or one or more drug container containing a liquid sclerosant composition.

Such kits may be packaged as a unit in a sterilized packaging.

In some examples, the drug containers comprising the liquid sclerosant composition may be squeezable drug containers. By squeezing of the container, it is made easier to introduce the liquid drug into the container without contamination. In other examples, syringes may be used for extracting a composition from the drug container and injecting it into the container for foaming.

In a further aspect, a method for preparing a foamed sclerosant composition is provided. The method comprises introducing a liquid sclerosant composition into a container according to any of the examples herein described, and then rotating the actuator to rotate the mixing element until a suitable foam has been obtained.

In some examples, rotating the actuator may comprise rotating the actuator with a varying speed. During the foaming process, varying the speed, e.g. a gradual increase may be beneficial. For example, in cases wherein a magnetic coupling is used between actuator and mixing element, a gradual increase can ensure that the magnetic coupling is maintained and effective between actuator and mixing element.

In some examples, physiological gases may be used, in other examples ambient air may be used. In some examples, glycerin may be added to the liquid composition before mixing.

In yet a further aspect, a foamed sclerosant composition is provided, obtainable by any of the methods herein described. The foamed sclerosant composition as obtained may be distinguished from foams obtained by Tessari's method in its bubble size and homogeneity, and its stability.

Another aspect of the present disclosure relates to the foamed sclerosant composition obtainable by any of the methods herein described, for use in the treatment of varicose veins, spider veins, or haemorrhoids. Thus, this aspect relates to the use of a sclerosant drug, for the manufacture of a foamed sclerosant composition obtainable by any of the methods herein described, for the treatment of varicose veins, spider veins; and may also be formulated as a method for the treatment of varicose veins, spider veins, or haemorrhoids, which comprises administering a therapeutically effective amount of the foamed sclerosant composition obtainable by any of the methods herein described, in a subject in need thereof, including a human.

BRIEF DESCRIPTION OF THE DRAWINGS

Non-limiting examples of the present disclosure will be described in the following, with reference to the appended drawings, in which:

FIGS. 1A-1E schematically illustrate an example of a mixing element which may be used in a variety of containers for producing a foamed sclerosant composition;

DETAILED DESCRIPTION

Figure 2A:
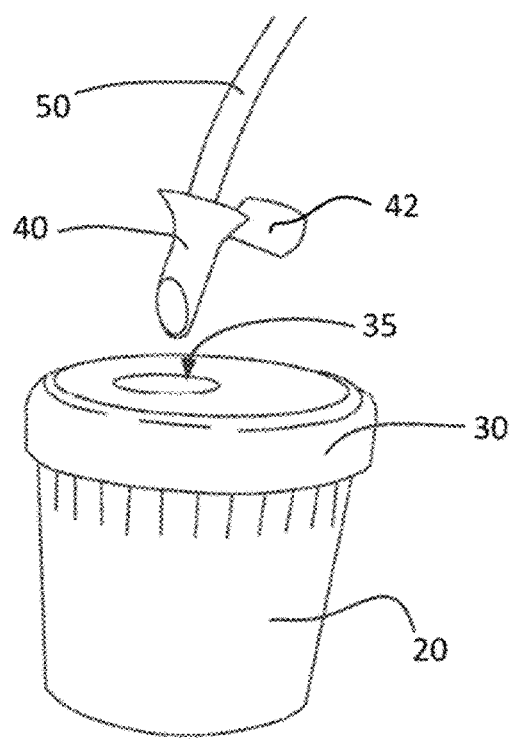
FIGS. 2A-2D schematically illustrate a container, and an introducer according to an example.
Figure 2B:
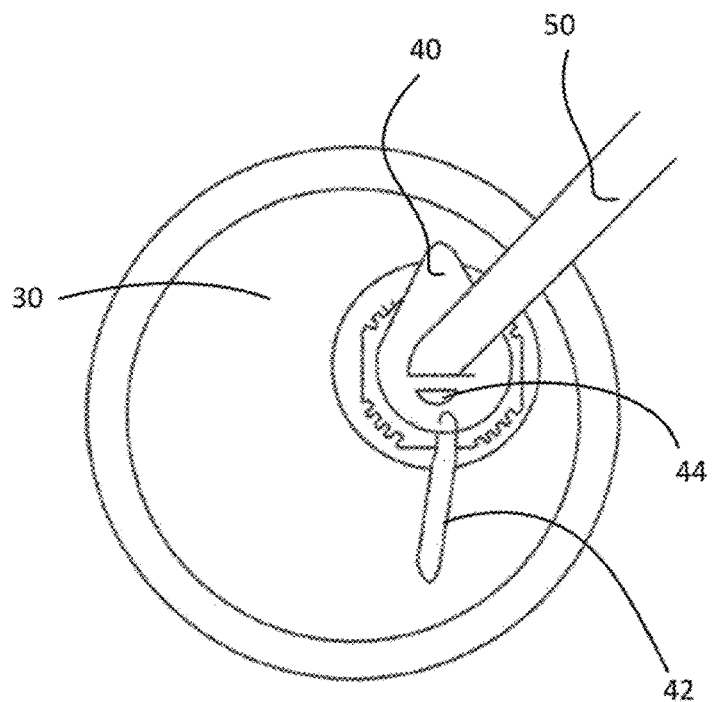
Figure 2C:
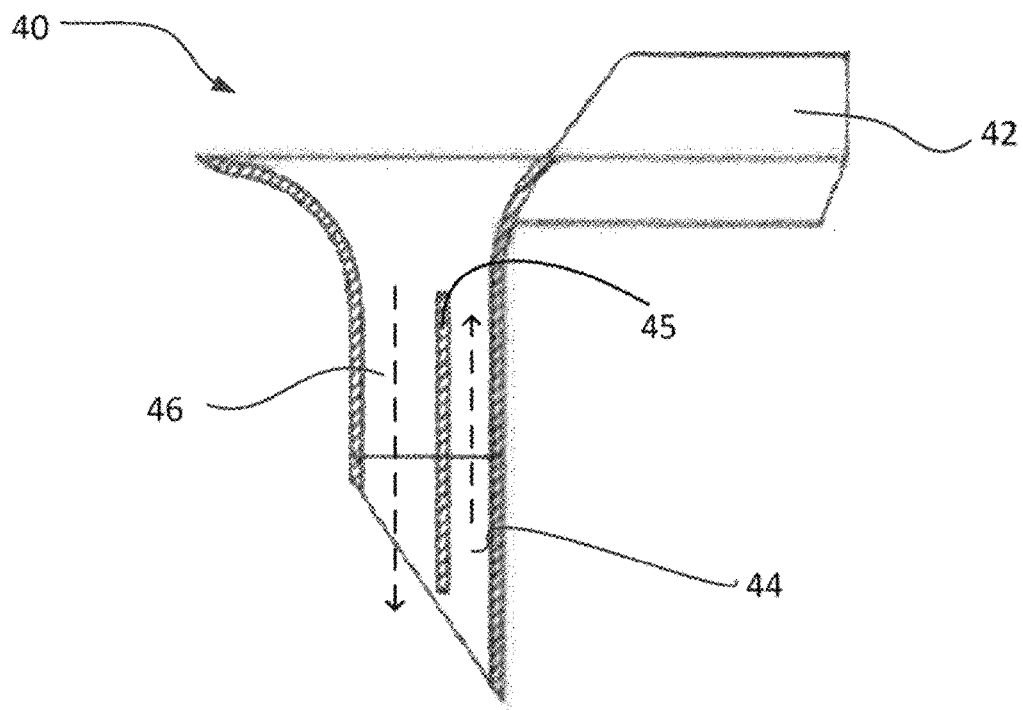

The expression "therapeutically effective amount" as used herein, refers to the amount of the foamed composition that, when administered, is sufficient to treat the diseases to which it is addressed. The specific dose of the foamed sclerosant composition to obtain a therapeutic benefit may vary depending on the particular circumstances of the case.

As previously mentioned, an aspect of the present disclosure relates to a foamed sclerosant composition obtainable by any of the methods herein described. The expression "obtainable by" is used herein for defining the foamed sclerosant composition by its preparation process. In particular, it refers to the foamed composition that can be obtained through the preparation process which comprises the steps of: introducing a liquid sclerosant composition into a container according to any of the examples described herein, and rotating the actuator to rotate the mixing element until a suitable foam has been obtained.

For the purposes of the present disclosure, the expressions "obtainable", "obtained" and similar equivalent expressions are used interchangeably and, in any case, the expression "obtainable" encompasses the expression "obtained".

Throughout the present disclosure, the terms sclerosant and sclerosing are used interchangeably. Similarly, sclerosing foam, and foamed sclerosant composition are used interchangeably as well.

For the purposes of the present disclosure, the term foamed sclerosing composition refers to a composition of a foam capable of bringing about a sclerosing effect, i.e. a composition for use as a medicament for intravenous injection, which is capable of causing an injury to the vessel wall by endothelial vacuolation of the epithelial cell membrane (the layer in contact with the bloodstream). Thus, the foamed sclerosing composition irritates the inner surface of the vein just producing the formed thrombus formation by platelets and aggregates. Similarly, the term liquid sclerosing composition refers to a composition in liquid form including a sclerosing agent. The liquid sclerosing composition forms an ingredient to obtain the foamed sclerosing composition.

The sclerosing compositions according to examples of the present disclosure comprise a sclerosing agent and also a suitable vehicle which can be injected without toxicity in the affected veins. In some examples, the liquid is selected from water (particularly distilled water) and physiological saline.

Examples of sclerosing agents that can be present in the sclerosing compositions of examples of the present disclosure include, without limitation, polidocanol, sodium tetradecyl sulfate, chromated glycerin, hypertonic saline, sodium morrhuate and sclerodex (hypertonic saline in combination with dextrose).

In a particular example, the sclerosing composition used comprises polidocanol and water. In another embodiment, the sclerosing composition further comprises glycerin.

In one particular example, the sclerosing composition may comprise a solution of a sclerosing agent, such as polidocanol, in a liquid, such as water or physiological saline, at a concentration from 2 mg to 20 mg in 1 mL liquid (which corresponds to 0.20-2.0%) (w/v). In another example, the sclerosing composition may comprise an solution of a sclerosing agent, such as polidocanol, in a liquid, such as water or physiological saline, at a concentration from 2 mg to 5 mg in 1 mL liquid (which corresponds to 0.20-0.50% (w/v)). With the devices and methods described herein, it has been found that even at very low concentrations e.g. 0.2% (w/v), still a stable foam may be obtained, contrary to e.g. Tessari's method.

In another particular example, the sclerosing composition may comprise a solution of polidocanol in water or physiological saline at a concentration of 5 mg/mL.

In another particular example, the sclerosing composition may comprise a solution of polidocanol in water or physiological saline at a concentration of 20 mg/mL.

In some examples, the foamed sclerosant composition may have a density of 0.07 g/mL-0.19 g/mL and a half life from 6.5±3 to 10.6±3 minutes.

FIGS. 1A-1E schematically illustrate an example of a mixing element which may be used in a variety of containers for producing a foamed sclerosant composition. FIG. 1A schematically illustrates a three-dimensional view of a mixing element. The mixing element in this example is a disc 10, that comprises a central opening 12 in which a magnetic element may be placed. The magnetic element or core may be kept in place between protrusions around the border of the central opening, shown in FIG. 1B.

The disc in this example has an outer ring 14 with vertically extending teeth 16. The portions 18 of the outer ring 14 may be of varying height as shown in this example. FIGS. 1C, 1D and 1E show respectively a side view, a top view and a cross-sectional view of the same disc.

The disc may be made of a non-magnetic material (apart from the magnetic core element). For example, a polymeric material may be used such as e.g. Polypropylene (PP) or Polytetrafluoroethylene (PTFE) or Nylon.

In other examples, instead of vertically extending teeth 16, horizontally extending teeth may be used. In some examples, instead of a central opening, a central housing may be provided in which the magnetic core element is contained.

FIGS. 2A-2D schematically illustrate a container, and an introducer according to an example. A mixing element according to the example of FIG. 1 may be used in combination with such a container.

Figure 2D:
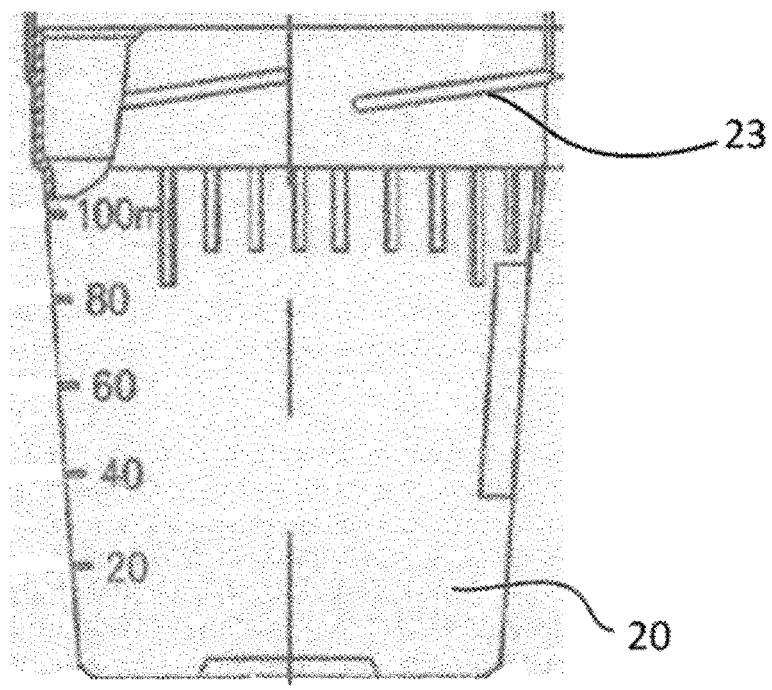

The container in this example comprises a container body 20, and a separate lid 30 for closing off the top of the container body. The separate lid may have e.g. a threaded coupling with the container body. This is illustrated in FIG. 2D. In the lid according to this example, a valve 35 is provided.

Valve 35 may be used for the introduction of the liquid sclerosant composition. The same valve may be used for the introduction of physiological gases e.g. a mixture of $O_2/CO_2$. For the introduction of the physiological gas, an introducer such as the one illustrated in FIGS. 2A-2C may be used.

The introducer 40 has a handle 42 by which the introducer may be held and manipulated. The introducer 40 in this example includes a cylindrical portion with a wedge-shaped or sharpened end. The wedge shaped end with one straight wall and an inclined wall enables an easier introduction into the valve of the container. The cylindrical portion and wedge of the introducer is divided by a central wall 45 into two different channels. A first channel 46 may serve for the introduction of the physiological gas. To this end, a tube 50 or nozzle from a gas cylinder may be introduced into channel 46. A second channel extends into the same container any serves to evacuate the gas inside the container.

The container 20 may be sterilized and packaged in a sterile packaging, e.g. a wrap. Enclosed within the container a mixing element can already be provided. For example, the disc with magnetic core of example 1 could be used.

In some of the experiments, a polymeric material container of polypropylene has been used, having a slightly conical shape having a height of 7 cm diameter, a basis of 5 cm diameter. The container in the illustrated example has a scale showing 20, 40, 60, 80 and 100 mL.

A standard magnetic stirrer which is frequently found in laboratories may be used as a rotating actuator. The container may be positioned on the magnetic stirrer which may comprise clamps to hold the container. The magnetic stirrer when running causes a rotating magnetic field. The rotating field may be created either by a rotating magnet or a set of stationary electromagnets. The rotating magnetic field drags along the magnetic core of the mixing disc and thereby sets it into rotation.

Experiments have been carried out using a magnetic stirrer with an analogic control type AGIMATIC® (code 7000242) without heating for speeds of 60 to 1600 rpm. It may comprise an upper plate of stainless steel (type 304 AISI®) having a diameter of 14.5 cm, wherein the container can be positioned. Is also has a security ring against spilling which consists of two 15 cm diameter plastic discs having a central opening of 5 cm, wherein the container can be placed.

The system can thus use sterile atmospheric air which is contained inside the container or a gas mixture based on a physiological composition based in a combination of $O_2/CO_2$. Depending on the varicose vein to be treated, depending on the profile of each patient and/or injected desired volume, it can be decided the use either air or gas mixture, without the need to opening the container.

This treatment can be applied to a large variety of type of varicosity, of size and of location, on an outpatient basis and without limitation in performing daily activities. From spider veins, varicose veins or capillaries subcutaneous veins to large volume varicose veins, practically all of them can be treated by the resulting foam.

Another aspect offered with a sclerotherapy technique performed with the foam in examples of the present disclosure may be that no fasting or any specific preparation of the patient is required. The patients who follow the treatment with anticoagulants therapy such as aspirin, clopidogrel or similar or with oral acenocoumarol type (Sintrom®) may not be required to suspend their treatment.

In accordance with an aspect, a sclerosant foam may be prepared substantially as follows:

a).—The sterile container packaging is opened. At this stage, the container is still closed with the lid, it contains sterile gas therein, as well as the rotatable disc with serrated edges (edges with decreasing thickness) that carries at the centre a magnet. The introducer is contained in the same packaging and may be prepositioned in the valve.

b).—Introducing the sclerosing agent previously selected through the valve located at the surface of the lid using the introducer inserted in the same valve, c).—A mix of physiological gases (in this example, 50/50 of $CO_2$ and $O_2$) can be introduced through the introducer nozzle (oxygen and carbon dioxide at different proportions), it may be necessary to introduce the gas into the container before the start of the whipping or the emulsification. The introducer may be used for this purpose. Regarding the source of gas mixture, typically a cylinder having a safety valve may be used. It can be adapted with a nasogastric tube extension with a maximum diameter of 5.3 mm. The tube can be introduced through the introducer into the container lid.

After a few seconds, e.g. three seconds from opening of the key of the gas cylinder, the air contained in the recipient will be replaced by the new selected gas as one output of 300 cc is calculated.

Then, the introducer may be removed again so the container is closed. At the same time, the gas mixture chosen is maintained in the container and will be the gas contained in the bubbles of the foam.

It has been found that it can be advantageous to increase the rotational speed of the magnetic stirrer gradually. Generally within three minutes enough stable foam has been formed.

In some examples, mixing is performed during 30 seconds-4 minutes, more particularly during 1 minute-3 minutes.

Once the foam has been formed, the lid can be removed and a syringe may be used for aspirating the foam. It has been found advantageous to start the aspiration of the foam from the central area of the container. It has been found that generally, the most homogeneous foam was located at or near the bottom of the container and in a central portion of the bottom.

The following specific examples with reference to FIGS. 3 and 4 serve to illustrate characteristics of the foamed sclerosant composition that may be obtained using examples the systems and methods of the present disclosure.

Example 1. Feasibility Study of the Process of the Present Invention and Comparative Test with the Tessari Method The Instituto de Química Avanzada de Cataluña (Advanced Chemistry Institute of Catalonia (IQAC)) which belongs to the Consejo Superior de Investigaciones Cientificas (CSIC) was hired to carry out the tests described in the following. The purpose of this study was to demonstrate the feasibility of a new manufacturing methods and systems of the composition in the form of standardized foam and to compare its characteristics to foams obtained with the Tessari method. In particular, foam stability and obtained physicochemical properties of the bubble were examined.
Materials and Methods In order to obtain the foamed compositions of the present disclosure as well as the comparative foams obtained by the Tessari method, etoxisclerol (polidocanol) was used at two different concentrations: 0.5% and 2% (weight/volume) in distilled water to create the foam detergent.

Two preparation methods were compared: preparation using a magnetic stirrer and magnetic mixing element in a container substantially as described with reference to FIGS. 1 and 2, and the Tessari method.

Experiments were performed with atmospheric air, and also using as a gas mixture $O_2/CO_2$ with volume proportion of 50/50. The gas mixture was obtained from a gas cylinder of 10 liters at 50% oxygen and 50% carbon dioxide at 90.2 bar pressure (Linde bottle No. 307 265).

In summary, the following experiments were performed for both the method of magnetic stirring and Tessari's method:

| Gas mixture | Concentration of sclerosing agent |
|---|---|
| Air | 0.5% |
| Air | 2% |
| $O_2/CO_2$ (50/50) | 2% |

Experiments performed using the Tessari method used syringes 10 cc of BD® and B/Braun® with conical luer-lock, i.e. threaded. As a three-way tap, the Discofix® model of B/Braun® was used and for each experiment 20 syringe passes were performed in order to mix gas and liquid (3 mL) maintaining a volume ratio liquid/gas fixed at ⅓.

For the manufacture of the foam using the magnetic stirrer, 3 mL of the aqueous solution of sclerosing agent (also etoxiesclerol) at 0.5% or 2% were introduced into a container containing a magnetic disc and the agitation was started at 300 rpm for 15 seconds up to 700 rpm for 15 seconds and 2 minutes at 1600 rpm. This was done both for the samples using (ambient) air and for the samples using the mixture of $O_2$ and $CO_2$. Once the emulsion was formed, 10 cc syringes of different brands BD® and B/Braun® were used for aspiration in order to perform the corresponding measurements.

Once the various foams were formed, they were placed on slides for a microscope. Spacers were placed at 60+/−10 microns and then a cover glass was located in it proper position.

Samples were photographed through a Zeiss microscope coupled to a Canon Power Shot S90 being seen through a lens of 2.5×. Images of 2428×1821 $micron^2$ were generated. Subsequently these images were homogeneously treated with the ImageJ program using the procedure "threshold" and the particles analysis with the setting: Size 150-infinity, 0.75-1 circularity and "include Holes". The results included more than 100 bubbles and the diameter of the bubbles was calculated using the flat projection of the image.

Figure 3A:
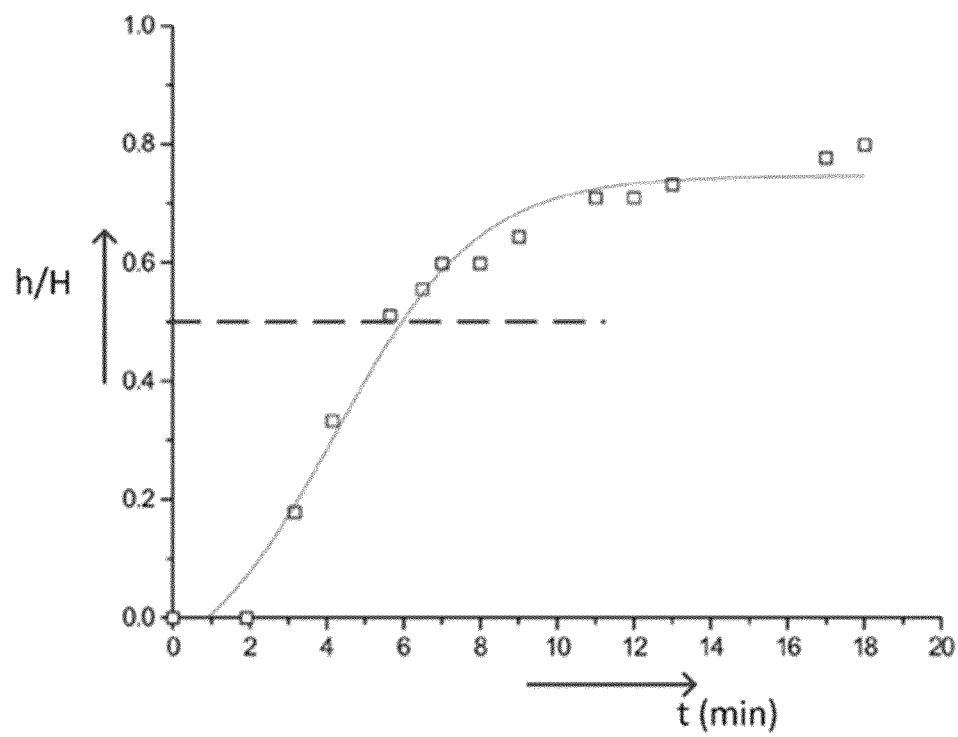
FIGS. 3A-3F schematically illustrate results of comparative tests on foams obtained with containers and methods according to the present disclosure and foam obtained with Tessari's method.
Figure 3B:
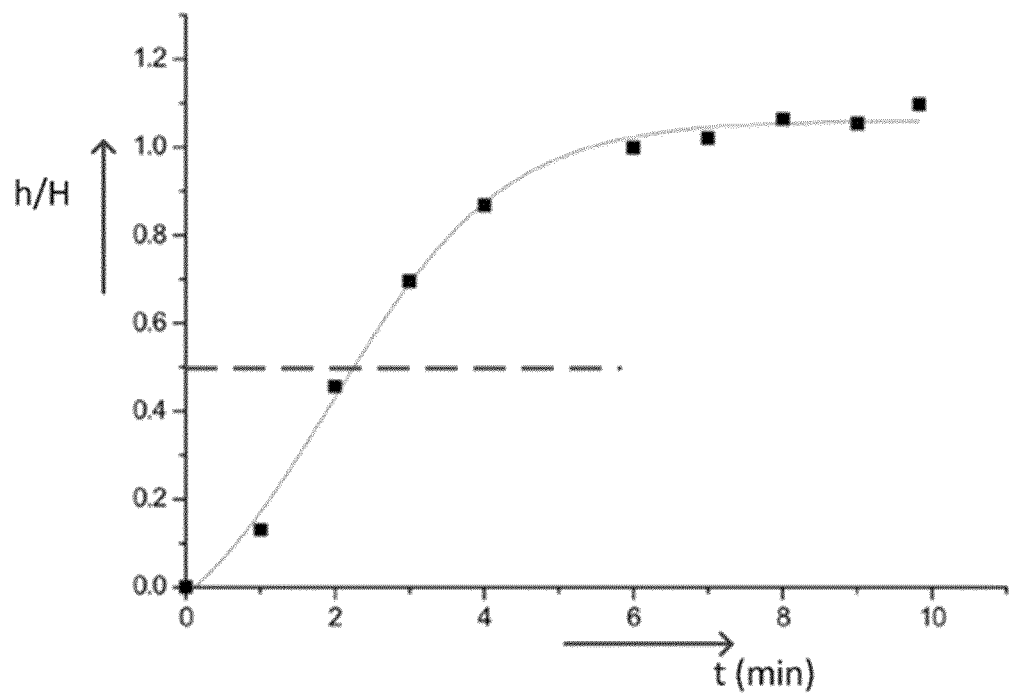
Figure 3C:
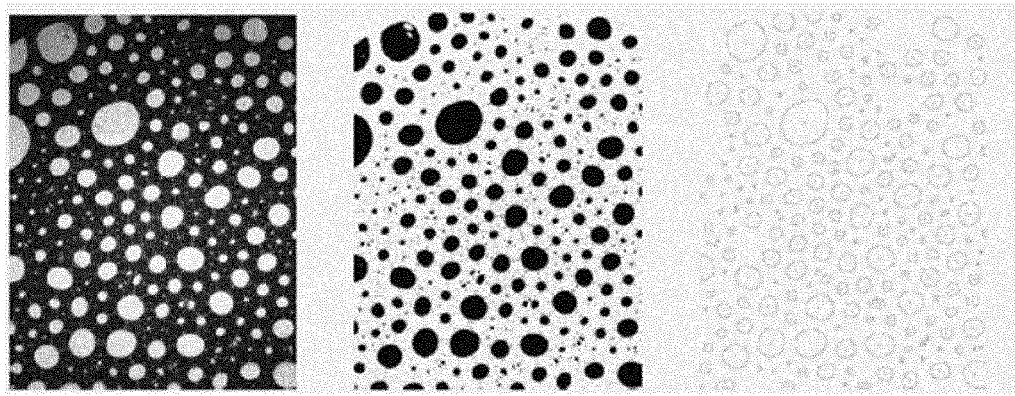
Figure 3D:
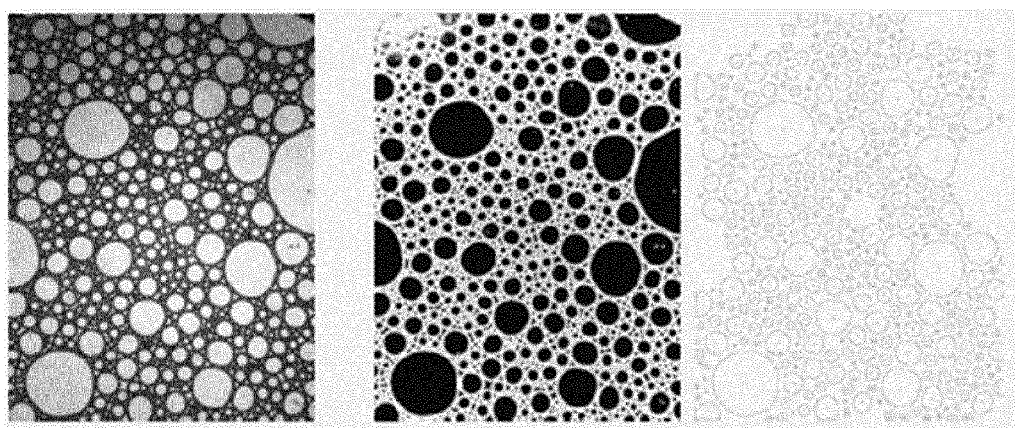
Figure 3E:
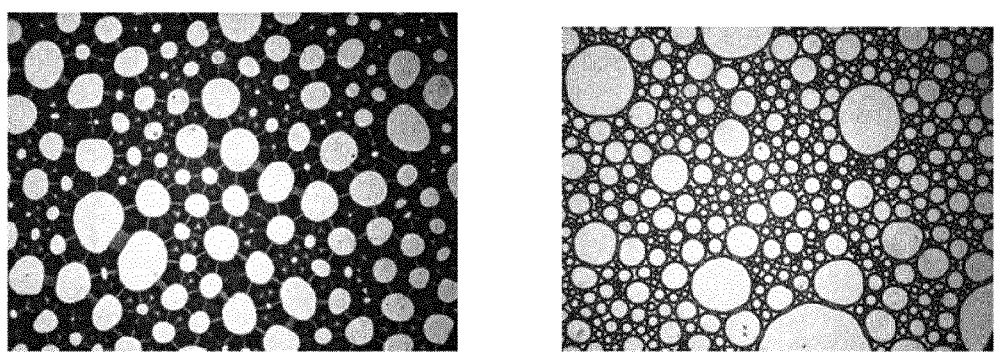

The obtained original foam images as well as the treated images corresponding to the foam of the invention are depicted in FIG. 3C. On the left side, the original image is shown, while on the right side, the treated image which was used for the calculation of bubble size is shown. The image in the middle is an image at an intermediate stage of the processing. The corresponding images for the foam obtained with the Tessari method are seen in FIG. 3D. FIG. 3E serves for a comparison of the original images on the left hand side of both foams (Tessari method on the right side and foam obtained using magnetic stirring on the left side).

Additionally, the half-life of the foam was calculated. The half-life was measured by placing syringes in an upright position against a dark background containing a stopwatch. Photographs were taken at a fixed distance every 30 seconds. The half-life was defined as the time necessary for half of the initial volume of sclerosant foam (which was determined from the weight of the foam) to become liquid. Using the ImageJ program, the height of the liquid versus time was determined and the relationship between this height and the initial foam height was calculated. The final height of liquid was determined from the fraction data in continuous phase volume of the foam which was determined from the volume of foam and its weight.

FIG. 3A shows the amount of liquid in the syringe over time for an example of the foam obtained with the magnetic stirrer using a concentration of 0.5% of etoxiesclerol and using air as gas. Reference sign H indicates the original height of the foam, whereas h indicates the height of the liquid and t is the time in minutes. From FIG. 3A, it can be derived that the foam according to this specific example showed a half-life time of approx. 5.9 minutes.

Similarly, FIG. 3B shows the same data for the comparative example of the foam obtained with the magnetic stirrer using a 2% concentration of etoxiesclerol with $O_2/CO_2$ (50/50) as gas. In this specific example, a half-life of approx. 2.2 minutes was measured.

To calculate the liquid/gas ratio in the foams obtained using the magnetic stirrer, the syringes were weighed before and after having been filled with foam using a high precision scale to the thousandth of a gram.

Figure 3F:
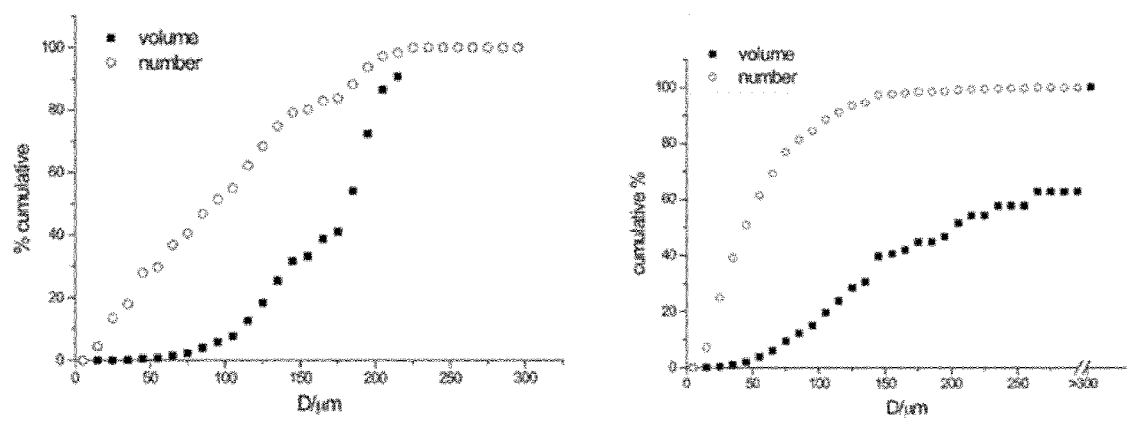

FIG. 3F shows a comparison of the distribution of bubble size for a foam obtained with a magnetic stirrer (on the left) and a foam obtained with Tessari's method (on the right).

The average size in number of bubbles obtained by the magnetic stirrer are $D=104\pm22$ μm and $\sigma=74\pm22$ μm and $65\pm20$ μm for etoxiesclerol at 2% with air and $O_2/CO_2$ respectively. Herein D is the diameter of the bubble, and a is the standard deviation of the diameter. The average size in number of bubbles obtained by the Tessari method are $D=51\pm20$ μm and $\sigma=40\pm20$ μm and $40\pm15$ μm for etoxiesclerol at 2% with air and $O_2/CO_2$ respectively.

CONCLUSIONS

With respect to the stability and half-life (Tm), the foams obtained using the magnetic stirring process showed a half-life of $6.5\pm3$ minutes for etoxiesclerol at 0.5% and $10.6\pm3$ minutes for etoxiesclerol at concentrations of 2% respectively using air as a gas in both cases.

Foams obtained using the Tessari method had a half life of $1.1\pm0.5$ minutes for etoxiesclerol at 0.5% and $2.0\pm0.5$ minutes for 2% concentration of etoxiesclerol using air. In both cases, a 95% confidence interval applies.

By using the mixture of gases ($O_2/CO_2$ 50/50) with etoxiesclerol concentrations of 2%, the half-life with the magnetic stirring system was $2.2\pm0.5$ minutes compared to $1.0\pm0.5$ minutes obtained by the Tessari method.

The liquid fraction of the foams prepared with the present method using ambient air are $0.093\pm0.0009$ for etoxiesclerol concentrations of 0.5% and $0.081\pm0.016$ for a concentration of etoxiesclerol of 2%. These fractions correspond to a ratio of liquid gas of approximately ⅑-¹/₁₀. When the mixture of $O_2/CO_2$ gas was used, a decrease in the gas until a ratio of ⅙ ($0.14\pm0.02$) was achieved.

Tessari method uses a default ratio ⅓ following some consensus or sclerotherapy guides.

Overall it was observed that the foams prepared with concentrations of 2% etoxiesclerol are more stable than those prepared with 0.5% etoxiesclerol, regardless of the gas mixture and the preparation method used. The foams that were prepared with air were consistently and significantly more stable than those prepared with the mixture of $O_2/CO_2$.

Interestingly, the measurements showed that the Tessari method generates smaller bubbles but with a greater dispersion resulting in greater average volume of bubbles in head of the present invention (see e.g. FIGS. 3C, 3D and 3F).

With respect to the bubble size, it has been found that the average bubble diameter prepared according to the magnetic stirring method are significantly different (at a level of 87%) according to the concentration of etoxiesclerol. The size of the foam at 0.5% showed an average diameter of $D=134\pm33$ μm, compared to $D=104\pm33$ μm of the 2% etoxiesclerol. The resulting bubble size is thus clearly sensitive to the etoxiesclerol concentration.

The standard deviation of the population measures has the same level of significance respectively ($109\pm21$ vs. $74\pm22$) where the relative width of the different populations corresponds to a probability of 91%. Additionally, the relative width for polidocanol concentration 0.5% is of 0.84 while the width for 2% of polidocanol is 0.70. (Statistical used: T tests)

With respect to the Tessari method, the average size by number of the bubbles is significantly lower than the average obtained by the magnetic stirring method $D=38\pm17$ μm. $\sigma=25\pm15$ for etoxiesclerol at 0.5%, and $D=51\pm20$ μm and $40\pm20$ μm for etoxiesclerol in a concentration of 2%. However the ratio of volume of the bubbles with respect to the total volume turns out to be higher for the Tessari method than for the magnetic stirring method disclosed herein. This is due to the heterogeneity of the foam obtained by the Tessari method: in spite of having a lower average diameter, there are also some significantly larger bubbles.

With the magnetic stirring method illustrated, a relatively homogenous foam, with increased stability as compared to the Tessari method (today's standard in the industry) can be obtained.

Figure 4A:
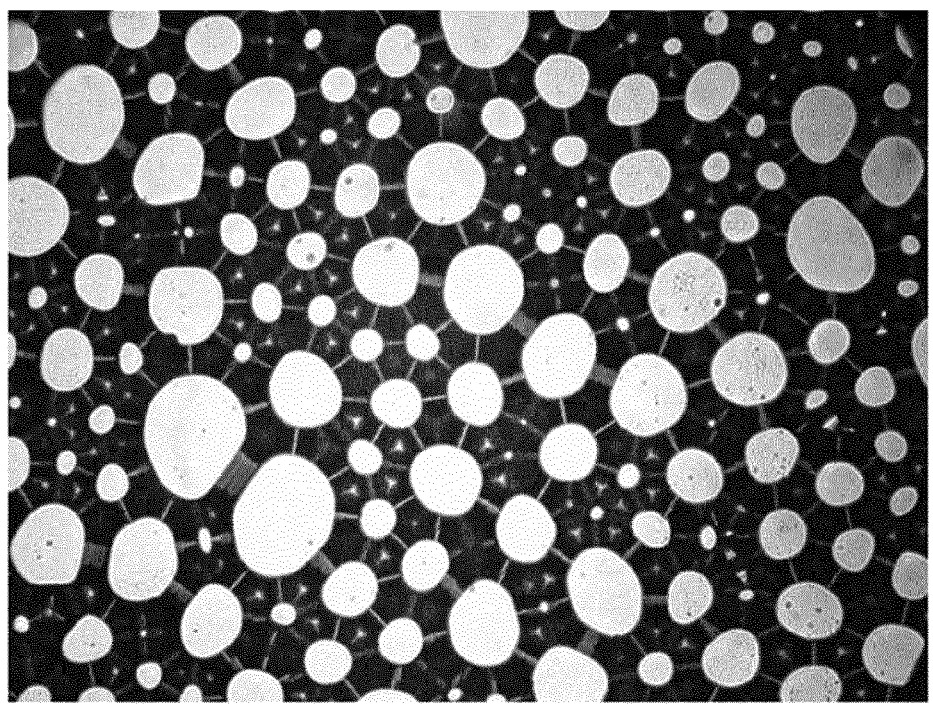
FIGS. 4A-4H schematically illustrate further results of comparative test.
Figure 4B:
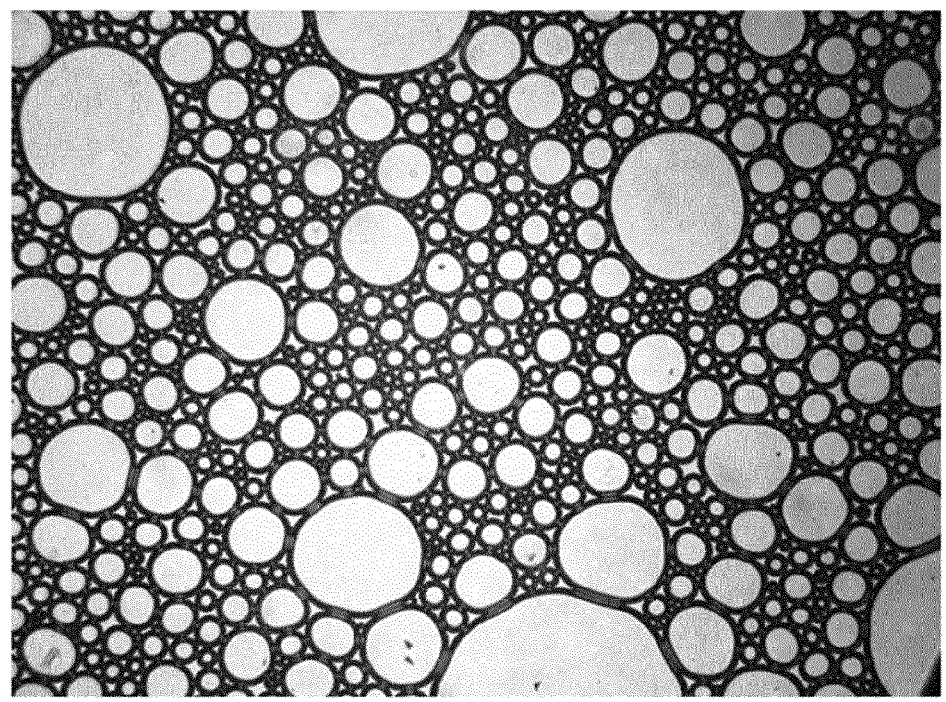

Some further experimental results are discussed with respect to FIGS. 4A-4H. FIGS. 4A and 4B show photographic images as obtained with a magnetic stirring method and Tessari's method respectively. A 2% concentration of etoxiesclerol in distilled water was used, with air as gas.

Figure 4C:
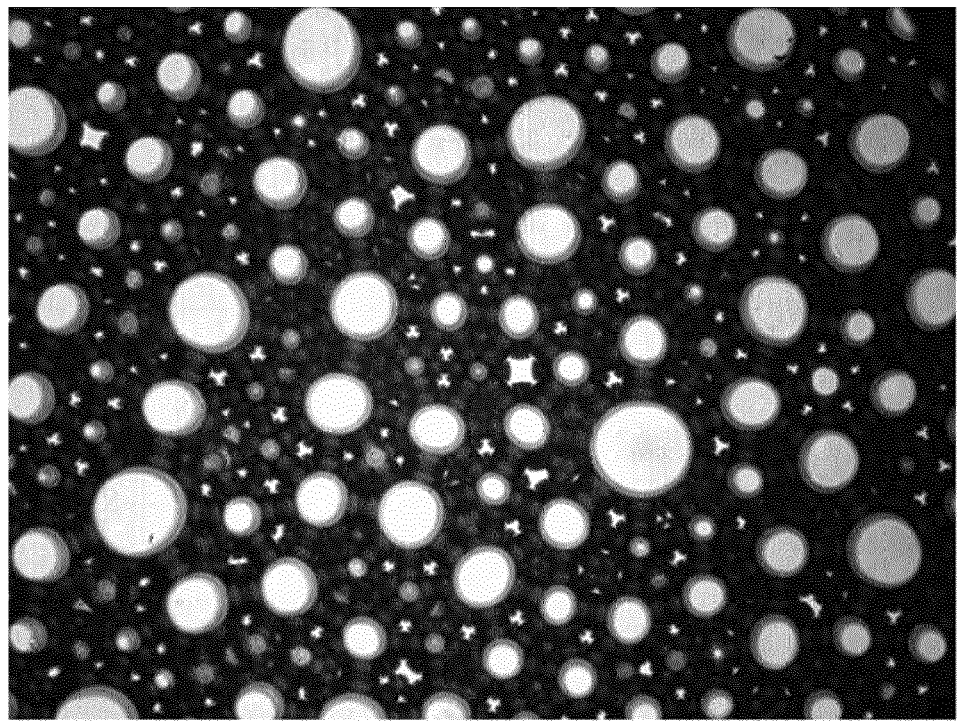
Figure 4D:
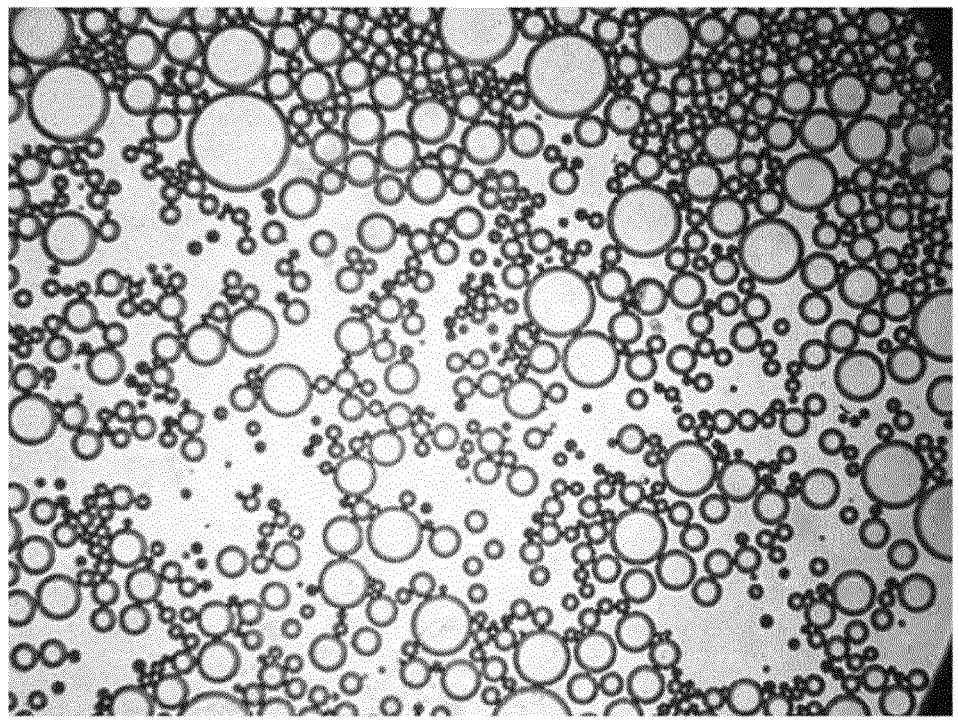

FIGS. 4C and 4D show photographic images as obtained with a magnetic stirring method and Tessari's method, respectively. A 2% concentration of etoxiesclerol in distilled water was used, with a mixture of $O_2$ and $CO_2$ as gas (volume ratio 50/50).

Figure 4E:
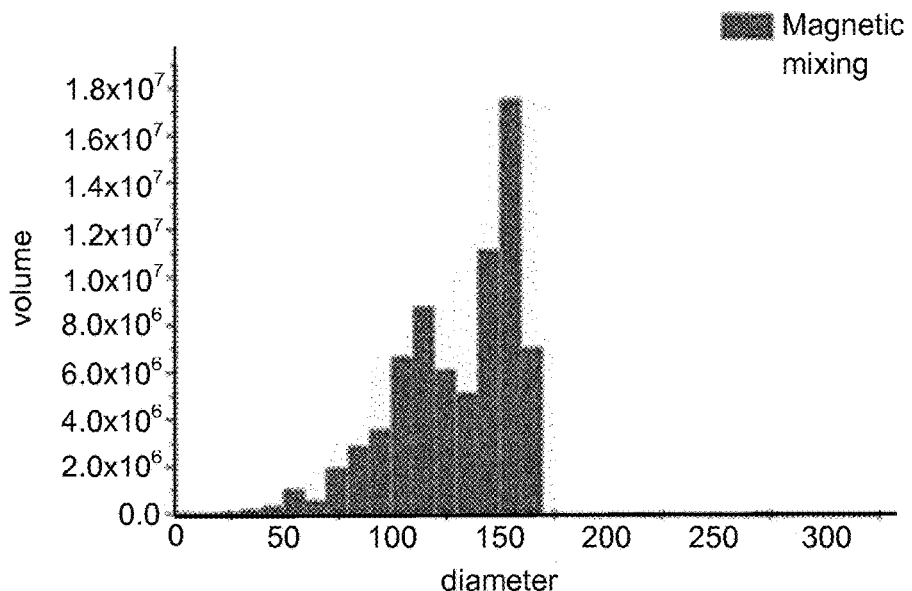
Figure 4F:
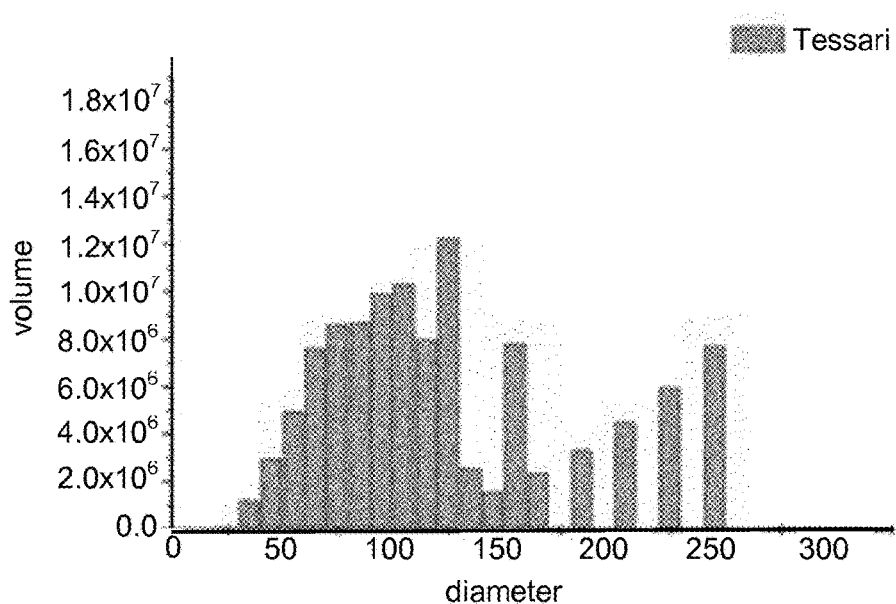
Figure 4G:
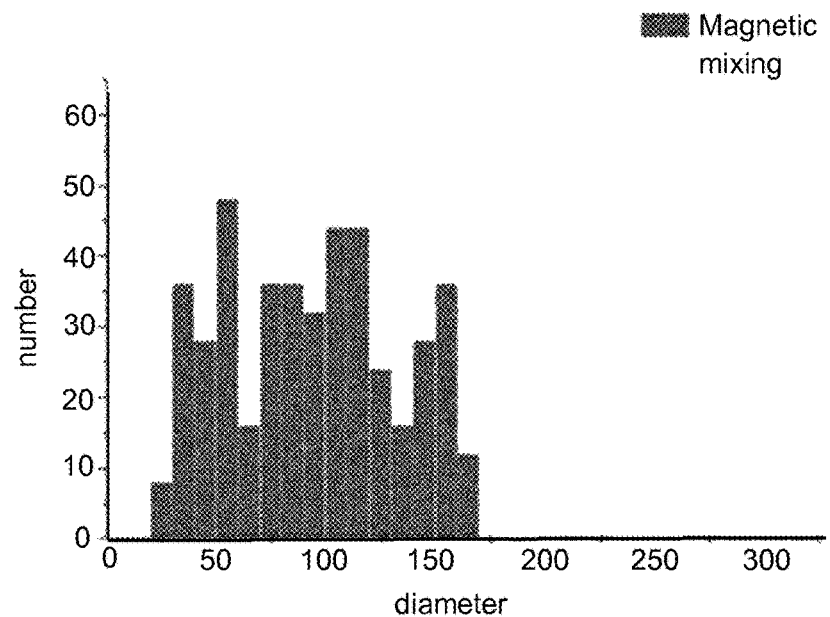
Figure 4H:
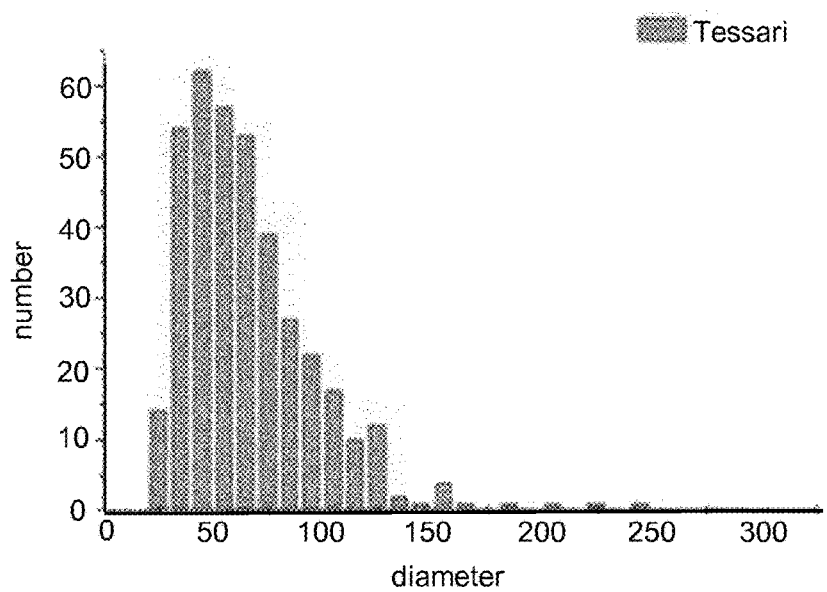

FIGS. 4E and 4F show the size distribution of the bubbles of the foam corresponding to images 4A and 4B respectively. FIGS. 4G and 4H show the size distribution of the bubbles of the foam corresponding to images FIGS. 4C and 4D respectively. In both cases, it may be seen that Tessari's method may lead to smaller average bubble size, but the foam is less homogeneous. The bubble range in the magnetic stirring methods is 50-150 whereas the bubble range in the Tessari methods is 25-245 The increased heterogeneity of the foam leads to coalescence and less stability.

FIGS. 5A-5H schematically illustrate another example of a container for preparing a foamed sclerosant composition. A container 100 is shown. A frangible portion 180 is provided in this example near the bottom of the container 100. After preparing the foam, the foam may be extracted by introducing a syringe though the port 180.

At the top of the container 100, a valve 125 is provided. The valve in this example has four leafs. It may be a one-way valve.

In the container a mixing element is provided. The mixing element in this example has a shaft 150. At a distal end of the shaft, a plurality of radially extending legs or "spokes" 152 is provided. They may be integrally formed with shaft 150. In an alternative example, the mixing element may comprise several separate components. For example, a separate shaft and foamer element (i.e. element in contact with liquid and gas to create the foam) may be provided. Also, the shaft in some examples could be split into several components.

The proximal end of shaft 150, has a slot 145 into which a shaft of a rotating actuator may be introduced. At the proximal end of the shaft, an upstanding flange 140 with horizontal extension 143 is provided. A ring shaped upstanding wall 148 may be integrally formed with the container body. The horizontal extension of flange 140 can be supported on the upstanding wall 148.

A rotating actuator may have a shaft with a distal end having a complementary shape to the slot formed in the proximal end of shaft 150. The horizontal extension 143 of flange 140 forms a friction bearing with the cylindrical upstanding wall 140. Suitable materials for the container body and the mixing element may be polymers, in particulars polymers having a low friction coefficient. Teflon or materials having a Teflon coating may be used in some examples.

Also in this example, the rotating actuator does not enter in the interior of the container body, i.e. in the foaming space. The foaming space is closed from the outside by the lid and the joint between upstanding flange 140 of the shaft 150 and the upstanding wall 148 of the lid. The foaming space may thus be virtually free of contamination. An aspect of this example is that higher rotational velocities may be achieved with the mixing element, since the coupling is mechanic rather than magnetic as in the previously illustrated examples.

Figure 5A:
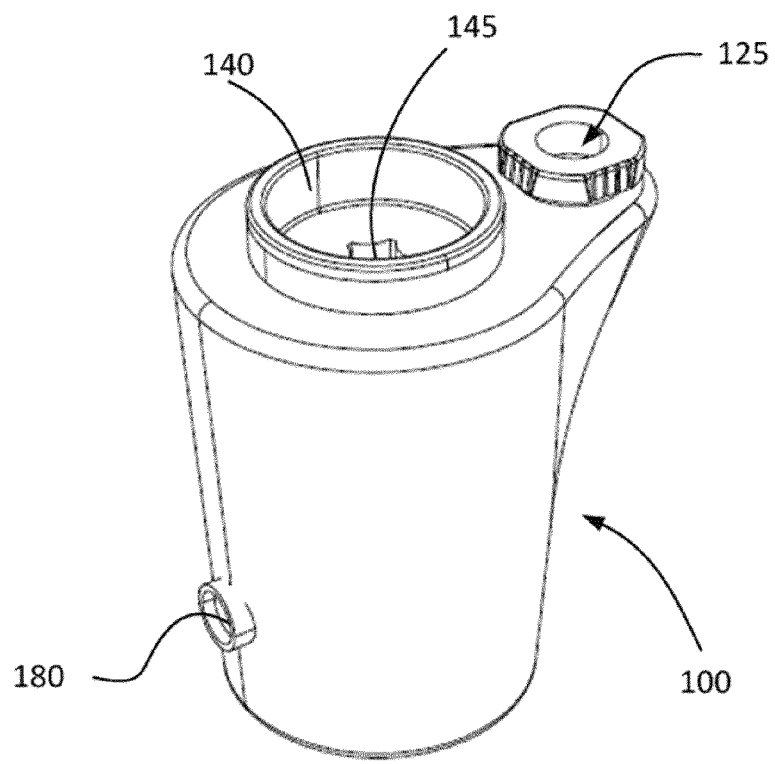
FIGS. 5A-5H schematically illustrate an example of a container and its components.
Figure 5B:
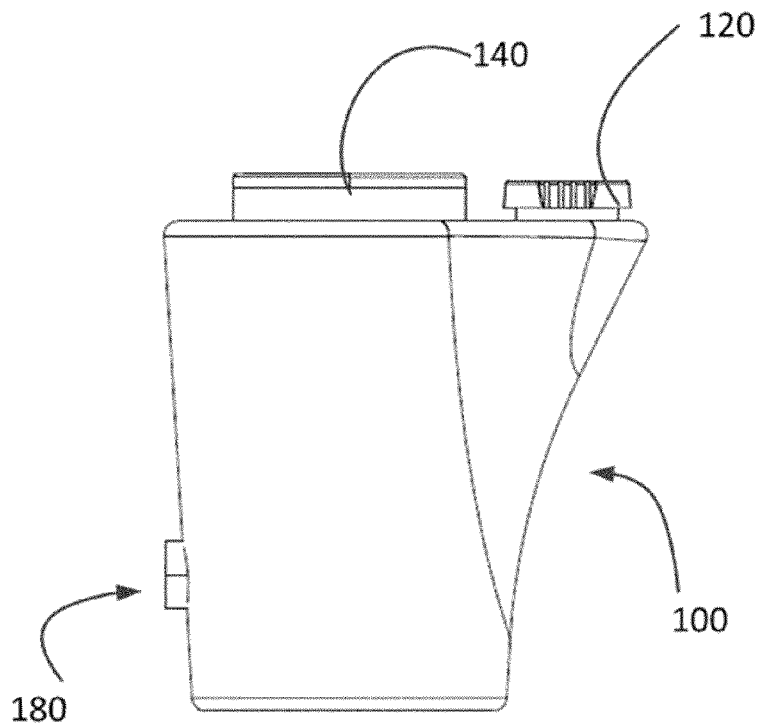
Figure 5C:
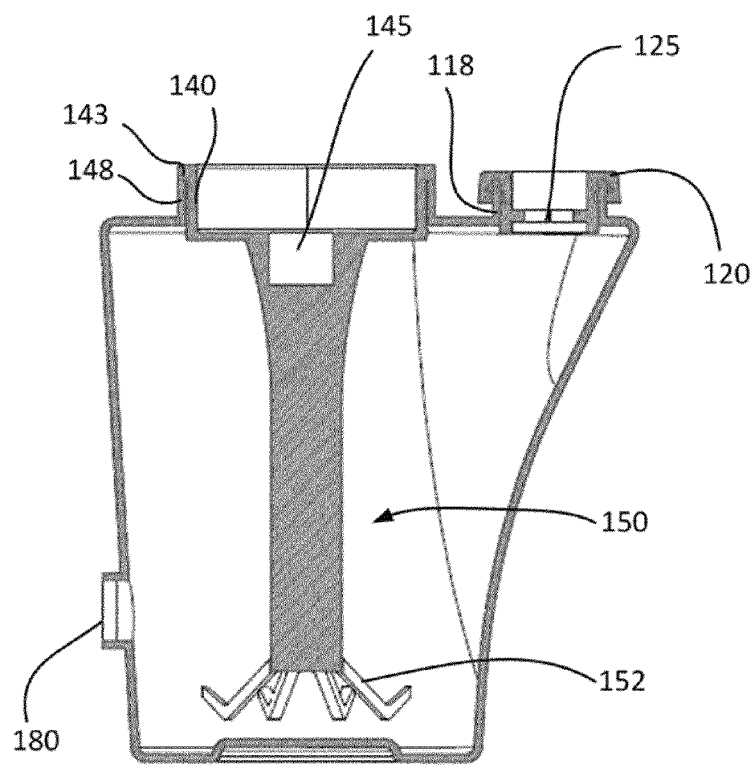
Figure 5D:
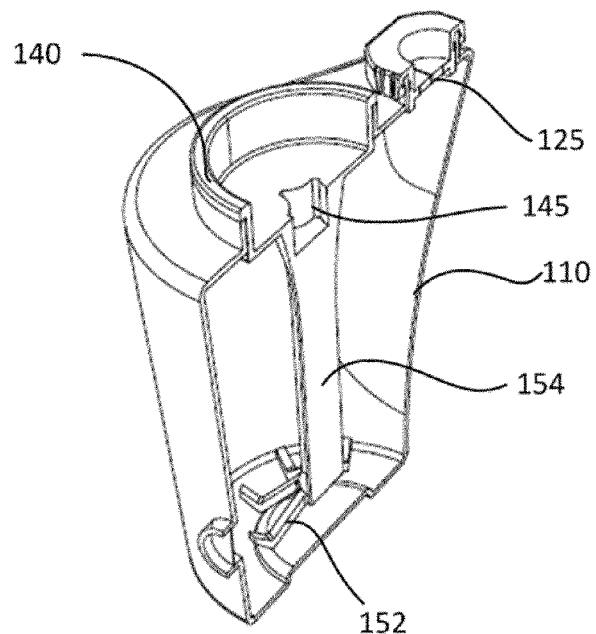
Figure 5E:
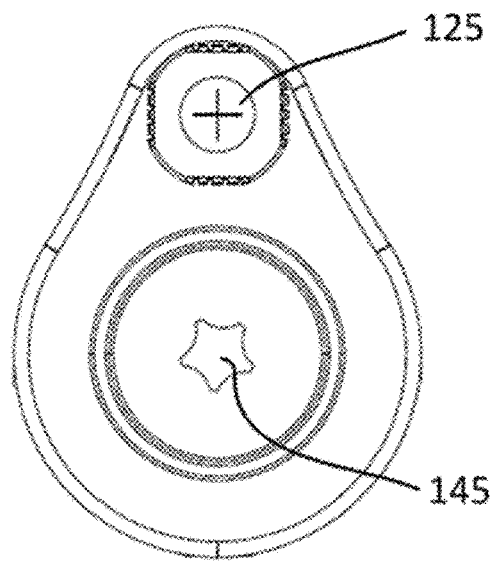
Figure 5F:
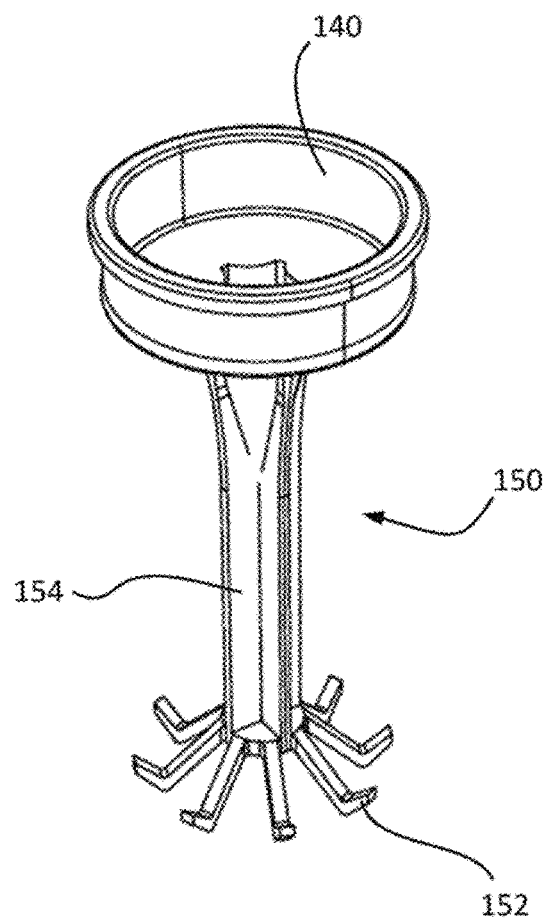
Figure 5G:
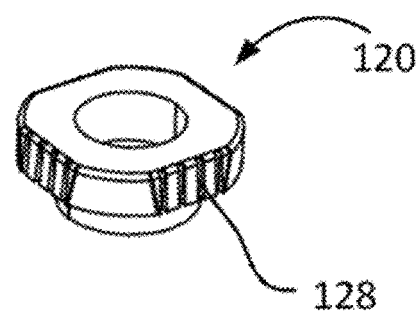

The top of the container body comprises another ring-shaped flange 118. A lid 120 comprising valve 125 may be attached at the ring-shaped flange. To this end, the lid 120 may comprise elastic fingers 128 which can be clipped around upstanding flange 118. Reference may be had to FIG. 5G.

The valve 125 may be used for introduction of the sclerosant composition in liquid form. The sclerosant composition may be introduced using a syringe. If the container of the sclerosant composition is squeezable, the composition may be directly introduced from the drug container to the container for foaming.

In examples wherein physiological gases are used for the creation of the foam, the same valve 125 may be used. A similar introducer as used in the example of FIGS. 1 and 2 could be used.

Figure 5H:
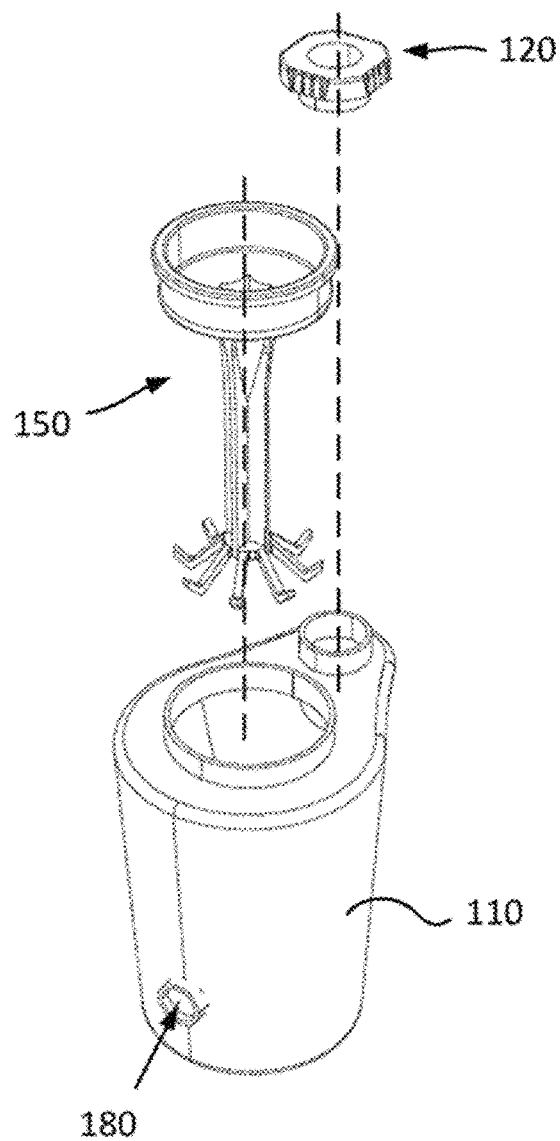
Figure 6A:
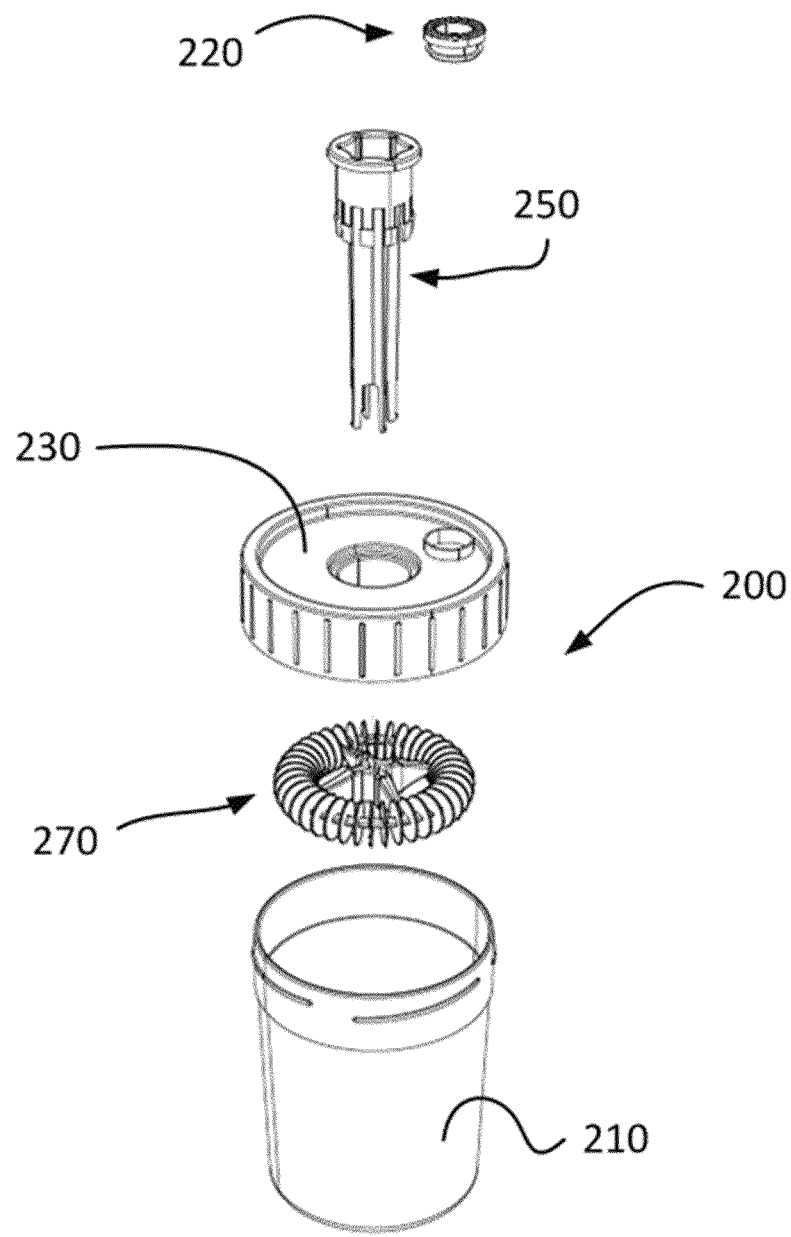
FIGS. 6A-6G schematically illustrate another example of a container and its components.
Figure 6B:
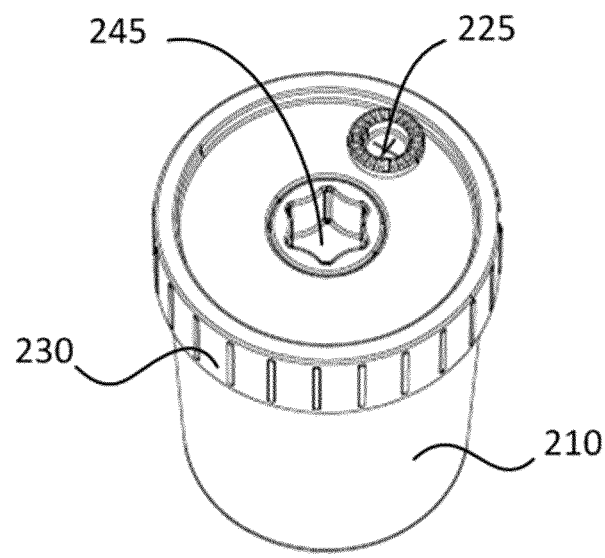
Figure 6C:
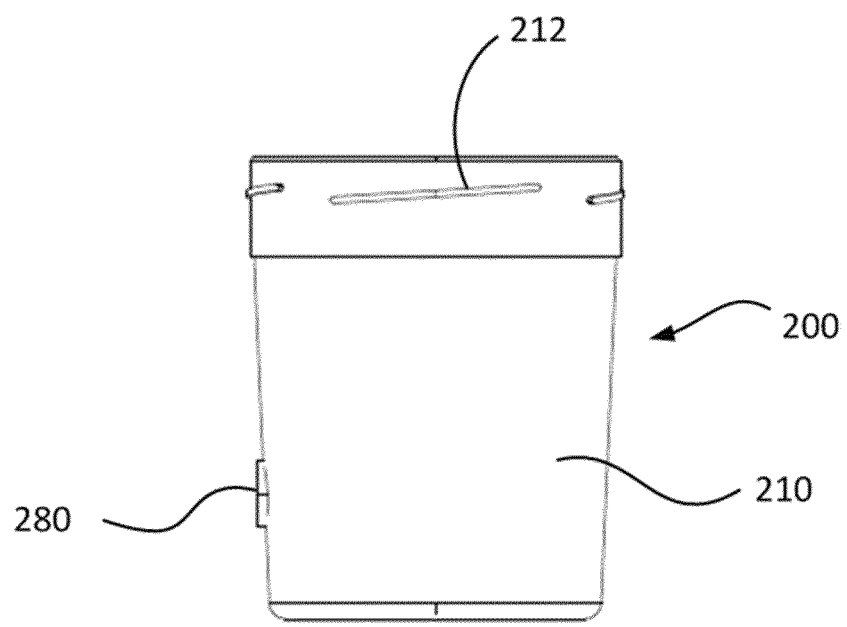
Figure 6D:
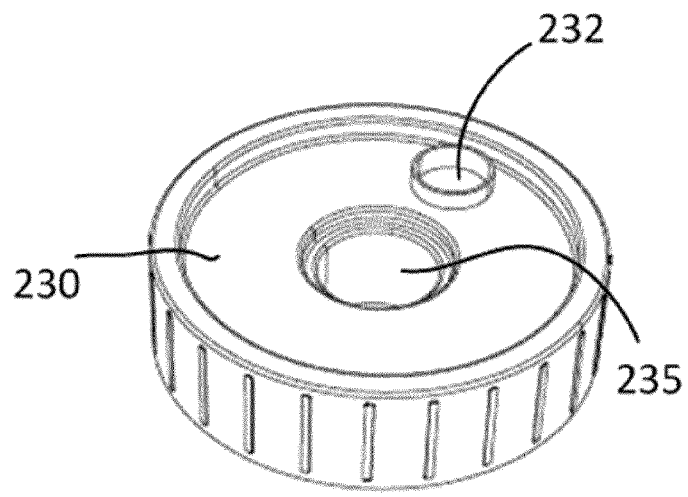
Figure 6E:
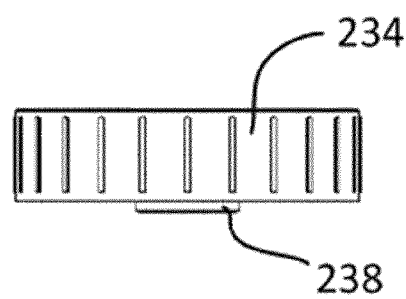
Figure 6F:
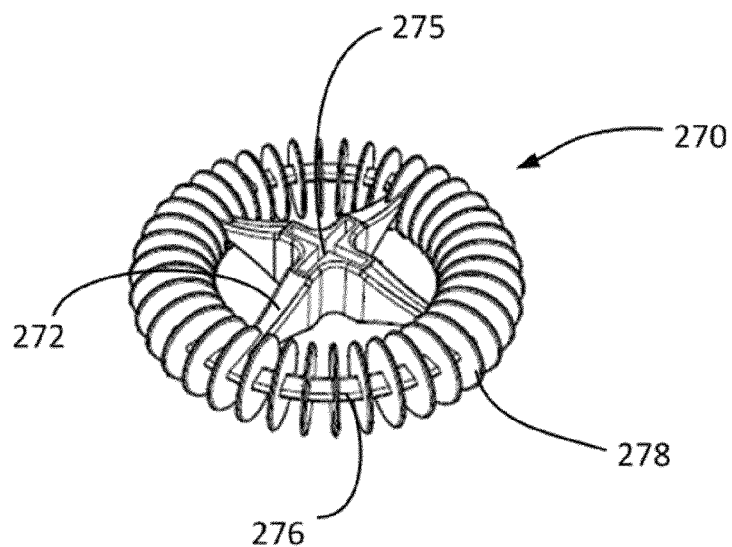
Figure 6G:
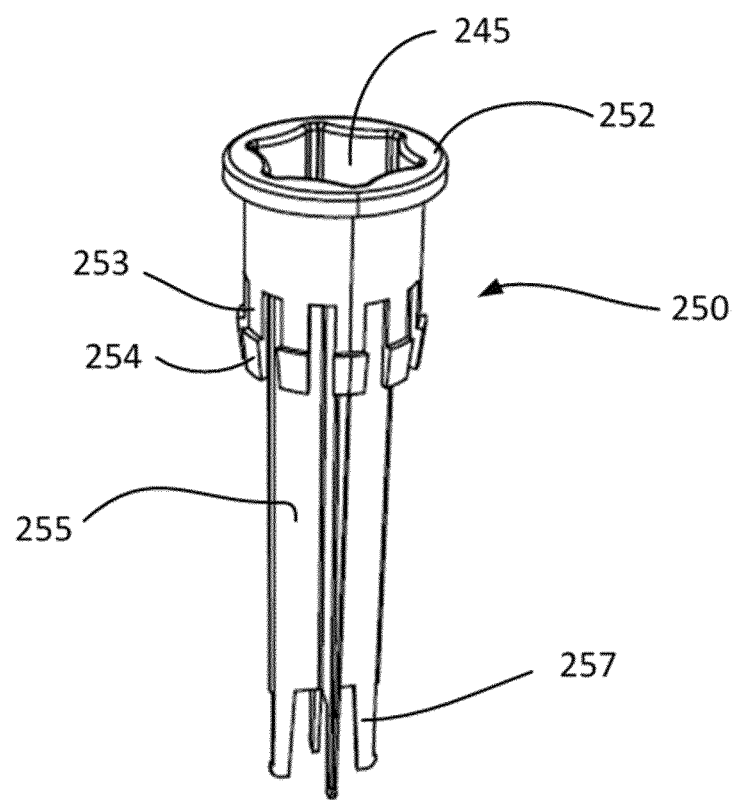

The components and assembly of container 100 may be seen in FIG. 5H. A container according to this example may comprise container body 110, mixing element 150 and lid 120 incorporating a valve.

The resulting assembled container may be packaged and sterilized. After opening of the package (e.g. wrap or foil), the container contains sterile air. In order to make the foam, the only possible contamination can become from the introduction of the liquid sclerosant composition. However, this contamination will be very limited. If physiological gases are used in the preparation of the foam, then also the contamination is very limited, since the quality of the physiological gas is also controlled. It may replace and contamination as it is introduced. To extract the foam, a syringe may be introduced through the port 180.

A further example of a container is schematically illustrated in FIGS. 6A-6G. In this example, a container 200 assembly comprises a container body 210, a lid 230 which can be screwed on the top of the container body, a mixing element which is composed of a shaft and foamer ring 270, and a lid with 220 carrying a valve 225.

Near the top of the container body 210 threads 212 are provided. Mating threads are provided on an internal surface of the lid 230. The lid 230 comprises a central opening 235 through which shaft 250 extends into the interior of the container body. The lid 230 may also comprises a further smaller opening 232 with a circular flange upon which valve lid 220 can be mounted.

Lid 230 in this example comprises a central cylindrical extension 238 extending downwards. Lid 230 may further comprise a grip portion 234 with increased roughness to facilitate gripping and rotating.

The mixing element in this example may comprise a shaft 250. A foamer ring 270 may be attached at the distal end of shaft 250. Shaft 250 may comprise four legs 255, and the foamer ring 270 may comprises a central slot 275 which has a shape complementary to the legs 255 of shaft 250.

The foamer ring may further comprise a circumferential ring 276 upon which a plurality of cylindrical discs 278 are mounted. In an alternative embodiment, instead of the discs on ring 276, a helical filament wound along a circle may be provided. Horizontal bridges 172 may connect ring 276 with slot 275.

Shaft 250 has a cylindrical portion with vertically extending fingers 253. At the ends of the fingers upstanding portions 254 may be provided. The fingers may be elastically deformable. As the shaft 250 is introduced into the central opening 235 of the lid 235, the fingers may be pushed slightly inwards. Once the upstanding portions 254 extend beyond the cylindrical central extension 238 of lid 230, the upstanding portions, due to the elastic deformability of fingers 253, move outwards. A clipping engagement of shaft 250 with lid 230 may thus be achieved.

As in the previous example, also a mechanical coupling between the rotating actuator and the shaft 250 of the mixing element is provided. Also in this example, the foaming space is substantially sealed off from the outside by the joint between the shaft 250 and cylindrical extension 238 of the lid. The rotating actuator from outside the sterile environment does not enter into the foaming space, thus reducing or avoiding any possible contamination. Contrary to the previous example, the lid as a whole may be removed from the container body. However, this is not necessary for aspirating the foam in examples wherein a port 280 is provided for aspirating the foam. As mentioned with respect to previous examples, port 280 may take the form of a frangible portion of the sidewall of the container body. In alternative examples, a port for aspiration may be arranged in the bottom of the container body.

Although only a number of particular examples have been disclosed herein, it will be understood by those skilled in the art that other alternative embodiments and/or uses and obvious modifications and equivalents thereof are possible. Furthermore, the various examples disclosed herein van be combined. The scope of the present disclosure should not be limited by any of the particular embodiments disclosed, but should be determined only by a fair reading of the claims that follow.

What is claimed is:

1. A method for preparing and injecting a foamed sclerosant composition, the method comprising:
obtaining an assembly for the production of a foamed sclerosant composition, the assembly comprising:
a sterilized container disposed inside a sterilized packaging, the sterilized container including a container body having an interior defined by one or more sidewalls extending between a top and a bottom of the container body, and
a sterilized mixing element disposed in the sterilized packaging inside the container body, wherein the sterilized mixing element is a disc comprising a central opening in which a magnetic element is placed, the magnetic element being fixed to the disc, the sterilized mixing element being free from physical attachment to any other part, a foaming space being formed in an interior of the container body between the one or more sidewalls and at least a portion of the sterilized mixing element,
wherein the sterilized mixing element is configured to be magnetically coupled with a rotating actuator located outside the interior of the container body when the sterilized container is removed from the sterilized packaging, wherein the actuator is a magnetic stirrer, wherein the sterilized container is configured for the introduction of a liquid sclerosant composition in the foaming space, and wherein the bottom of the container body is configured to be positioned on the magnetic stirrer such that the magnetic stirrer when running causes a rotating magnetic field thereby dragging along the magnetic element of the disc and setting the disc into rotation, removing the sterilized container containing the sterilized mixing element from the sterilized packaging;

introducing a liquid sclerosant composition into the foaming space, positioning the container body onto a magnetic stirrer, running the rotating actuator magnetic stirrer at a varying speed to rotate the mixing element until the foamed sclerosant composition has been obtained, aspirating the foamed sclerosant composition from the container using a syringe; and injecting the aspirated foamed sclerosant composition into a patient using the syringe.

2. The method according to claim 1, wherein the disc has a circumference and comprises teeth around the circumference.

3. The method according to claim 1, further comprising a valve configured for the introduction of a liquid sclerosant composition the valve arranged to open towards the interior of the container body.

4. The method according to claim 1, wherein the sterilized container includes a valve for introduction of a physiological gas.

5. The method according to claim 4, wherein the sterilized container includes a first valve configured for the introduction of a liquid sclerosant composition the valve arranged to open towards the interior of the container body, the assembly further comprising a second valve for introduction of a physiological gas, wherein the second valve for the introduction of a physiological gas is the same as the first valve for the introduction of the liquid sclerosant agent.

6. The method according to claim 1, wherein the container body further comprises an exit for extraction of the foamed sclerosant composition.

7. The method according to claim 6, wherein the exit for extraction of the foamed sclerosant composition is a tearable portion of the container body.

8. The method according to claim 6, wherein the exit is arranged at or near the bottom of the container body.

9. The method according to claim 1, wherein the assembly further comprising comprises a lid to close off the top of the container body.

10. The method according to claim 1, wherein a lid is integrally formed with the container body.

11. The method according to claim 1, wherein the running the magnetic stirrer comprises running the magnetic stirrer at a speed of rotation between 60 and 1,800 RPM.

12. The method according to claim 1, further comprising introducing a mixture of physiological gases into the interior of the container body before running the magnetic stirrer.

13. The method according to claim 3, wherein the valve is a one-way valve arranged to open towards the interior of the container body.

14. The method according to claim 1, wherein the foaming spaced contains atmospheric air during the preparation of the foamed sclerosant composition.

15. The method according to claim 1, wherein the introducing a liquid sclerosant composition into the foaming space includes using an introducer defining a first channel for introducing of a physiological gas into the interior of the container body, and a second channel for evacuating a gas out of the interior of the container body.

16. The method according to claim 1, wherein the liquid sclerosant composition comprises distilled water or a saline.

17. The method according to claim 1, wherein introducing the liquid sclerosant composition into the foaming space includes squeezing a drug container containing the liquid sclerosant composition.

* * * * *